(12) United States Patent
Saxena et al.

(10) Patent No.: US 9,839,602 B2
(45) Date of Patent: Dec. 12, 2017

(54) PERSONAL CARE COMPOSITIONS CONTAINING CROSSLINKED SILICONE POLYMER NETWORKS AND THEIR METHOD OF PREPARATION

(71) Applicant: Momentive Performance Materials Inc., Waterford, NY (US)

(72) Inventors: Anubhav Saxena, Bangalore (IN); Monjit Phukan, Bangalore (IN); Tushar Navale, Mumbai (IN); Sigfredo Gonzalez, Danbury, CT (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 14/572,132

(22) Filed: Dec. 16, 2014

(65) Prior Publication Data

US 2016/0166497 A1    Jun. 16, 2016

(51) Int. Cl.
| | | |
|---|---|---|
| C08G 77/24 | (2006.01) |
| A61K 8/899 | (2006.01) |
| A61K 8/92 | (2006.01) |
| A61Q 17/04 | (2006.01) |
| A61Q 1/02 | (2006.01) |
| A61Q 19/00 | (2006.01) |
| C08K 3/38 | (2006.01) |
| C08L 83/06 | (2006.01) |
| C08L 83/08 | (2006.01) |
| C08K 3/22 | (2006.01) |
| C08K 3/34 | (2006.01) |

(52) U.S. Cl.
CPC .............. *A61K 8/899* (2013.01); *A61K 8/92* (2013.01); *A61Q 1/02* (2013.01); *A61Q 17/04* (2013.01); *A61Q 19/00* (2013.01); *A61K 2800/10* (2013.01); *A61K 2800/95* (2013.01); *C08K 3/346* (2013.01); *C08K 2003/2241* (2013.01); *C08K 2003/382* (2013.01); *C08L 83/06* (2013.01); *C08L 83/08* (2013.01)

(58) Field of Classification Search
CPC . C08L 83/06; C08L 83/08; C08K 2003/2241; C08K 2003/382; C08K 3/346; A61K 8/899; A61K 8/92; A61Q 1/02; A61Q 17/04; A61Q 19/00
See application file for complete search history.

(56) References Cited

U.S. PATENT DOCUMENTS

| | | |
|---|---|---|
| 3,159,601 A | 12/1964 | Ashby |
| 3,159,662 A | 12/1964 | Ashby |
| 3,220,972 A | 11/1965 | Lamoreaux |
| 3,445,420 A | 5/1969 | Kookootsedes et al. |
| 3,715,334 A | 2/1973 | Karstedt |
| 3,775,452 A | 11/1973 | Karstedt |
| 3,814,730 A | 6/1974 | Karstedt |
| 4,256,870 A | 3/1981 | Eckberg |
| 4,279,717 A | 7/1981 | Eckberg et al. |
| 4,465,818 A | 8/1984 | Shirahata et al. |
| 4,562,096 A | 12/1985 | Lo et al. |
| 4,987,169 A | 1/1991 | Kuwata et al. |
| 5,354,796 A | 10/1994 | Creecy et al. |
| 5,493,041 A | 2/1996 | Biggs et al. |
| 5,629,387 A | 5/1997 | Frances et al. |
| 5,654,362 A | 8/1997 | Schulz, Jr. et al. |
| 5,663,752 A | 9/1997 | Imamura et al. |
| 5,760,116 A | 6/1998 | Kilgour et al. |
| 5,811,487 A | 9/1998 | Schulz, Jr. et al. |
| 6,296,869 B1 | 10/2001 | Crotty et al. |
| 6,423,322 B1 | 7/2002 | Fry |
| 6,461,597 B1 * | 10/2002 | Morita ............... A61K 8/025 424/401 |
| 6,531,540 B1 | 3/2003 | O'Brien |
| 7,381,769 B2 | 6/2008 | O'Brien |
| 7,687,574 B2 | 3/2010 | Lu et al. |
| 7,833,541 B2 | 11/2010 | Lu et al. |
| 8,697,829 B2 | 4/2014 | Saxena et al. |
| 8,703,881 B2 * | 4/2014 | Saxena ............... A61K 8/896 525/477 |
| 8,772,422 B2 * | 7/2014 | Saxena ............... C08G 77/38 525/474 |
| 2007/0107141 A1 * | 5/2007 | Nguyen ............... A61K 8/8158 8/405 |
| 2013/0171080 A1 | 7/2013 | Sarkar et al. |
| 2013/0172192 A1 | 7/2013 | Saxena et al. |
| 2013/0172193 A1 * | 7/2013 | Saxena ............... A01N 25/10 504/360 |
| 2013/0172419 A1 | 7/2013 | Saxena et al. |

(Continued)

FOREIGN PATENT DOCUMENTS

| | | |
|---|---|---|
| JP | 06-247835 A | 2/1993 |
| JP | 06-247827 A | 9/1994 |
| WO | 00/08087 A1 | 2/2000 |

OTHER PUBLICATIONS

J.L. Spier, "Homogeneous Catalysis of Hydrosilation by Transition Metals, In Advances in Organometallic Chemistry", vol. 17, (1979) pp. 407-447, F.G.A. Stone & R. West Editors, Academic Press.
U.S. Appl. No. 14/572,139 for Applicants Alok Sarkar et al. filed Dec. 16, 2014.
U.S. Appl. No. 14/572,118 for Applicants Monjit Phukan et al. filed Dec. 16, 2014.

(Continued)

*Primary Examiner* — Margaret Moore
(74) *Attorney, Agent, or Firm* — Joseph S. Ostroff

(57) ABSTRACT

The invention is directed to a personal care composition which contains an ionically-modified cross-linked silicone network which is formed by the polymerization of a silicone polymer containing hydrosilylation effective unsaturated moiety, silyl hydride moiety and ionic radicals.

27 Claims, 3 Drawing Sheets

(56) References Cited

U.S. PATENT DOCUMENTS

| | | |
|---|---|---|
| 2013/0172427 A1 | 7/2013 | Saxena et al. |
| 2013/0172510 A1 | 7/2013 | Saxena et al. |
| 2014/0017188 A1 | 1/2014 | Sarkar et al. |
| 2014/0031734 A1 | 1/2014 | Saxena et al. |

OTHER PUBLICATIONS

U.S. Appl. No. 14/572,108 for Applicants Monjit Phukan et al. filed Dec. 16, 2014.
International Search Report dated Mar. 14, 2016.

* cited by examiner

PERSONAL CARE COMPOSITIONS CONTAINING CROSSLINKED SILICONE POLYMER NETWORKS AND THEIR METHOD OF PREPARATION

FIELD OF THE INVENTION

The present invention relates to silicone polymers, specifically crosslinked silicone polymers that have the benefits of compatibility with hydrophilic components and solid particulates in personal care compositions and the resultant personal care applications.

BACKGROUND OF THE INVENTION

The personal care industry thrives on being able to deliver multiple performance products based on mixtures of several components, with each having performance characteristics important to or desirable in the final formulation. One desirable characteristic is the ability to provide a silky initial feel in the formulation.

Silicone copolymer gels are known in the personal care industry for many uses including their use in skin care applications. However these gels often fail to provide the desired degree of wash-off resistance, pigment dispersibility and anti-whitening properties.

In addition, such silicone copolymer gels have typically been made by methods of generating crosslinked siloxane polymers that limit the range of desirable organofunctional groups that may be incorporated into the polymeric structure to create additional performance advantages in complex formulations.

SUMMARY OF THE INVENTION

The invention is directed to a personal care composition which contains an ionically-modified cross-linked silicone network gel in the oil phase of the personal care composition. The ionically-modified cross-linked silicone network used to make the cross-linked silicone network gel is chosen from cross-polymers formed by the hydrosilylation of a hydride-functional silicone containing at least two Si—H groups with an olefin containing at least two Si-olefinic groups, in the presence of a precious metal catalyst and optionally a solvent and, wherein one or more of the hydride-functional silicone, the olefin or the hydrosilylation neutral solvent contains an ionic radical moiety.

In one embodiment herein there is provided a personal care composition comprising an oil phase wherein the oil phase contains an ionically-modified cross-linked silicone network gel.

In one other embodiment herein there is provided a process of preparing a personal care composition comprising an oil phase wherein the process comprises adding an ionically-modified cross-linked silicone network gel to the oil phase of a personal care composition wherein the ionically-modified crosslinked silicone network gel is made by the process of reacting:

i) at least one silicone hydride bearing at least two Si—H residues,
ii) at least one cross-linker with two or more Si-unsaturated radicals,
iii) an effective amount of precious metal catalyst suitable for facilitating addition cure reaction between (a) and b, and
iv) optionally, a solvent suitable for swelling the said cross-polymer;

subject to the limitation that at least one of (i), (ii) or (iv) is selected from an ionically modified silicone of general formula (I):

$$M^1_a M^2_b M^3_c D^1_d D^2_e D^3_f T^1_g T^2_h T^3_i Q_j \qquad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ where $R^1$, $R^2$, $R^3$, $R^5$, $R^6$, $R^8$, $R^9$, $R^{10}$, $R^{11}$, $R^{13}$, $R^{15}$, $R^{16}$ are aliphatic, aromatic or fluoro containing monovalent hydrocarbon radicals containing from 1 to about 60 carbon atoms, specifically from 1 to about 20 carbon atoms and more specifically from 1 to about 8 carbon atoms;

where $R^4$, $R^{12}$, $R^{17}$ are monovalent or multi-valent radical bearing ion-pairs, where $R^7$, $R^{14}$ and $R^{18}$ are independently selected from hydrogen, —$OR^{20}$ and an unsaturated monovalent radical, wherein each $R^{20}$ is independently selected from hydrogen, and a monovalent hydrocarbon radical of from 1 to about 60 carbon atoms, where the subscripts a, b, c, d, e, f, g, h, i, j are zero or positive subject to the following limitations: the sum a+b+c+d+e+f+g+h+i+j is greater than or equal to 2 and less than or equal to 6000, and b+e+h is greater than 0 to form an ionically-modified crosslinked silicone network; and, shearing the crosslinked ionic silicone network during and/or after the reacting step with at least solvent (iv) to form the crosslinked ionic silicone network gel.

DETAILED DESCRIPTION OF THE INVENTION

Figure 1:
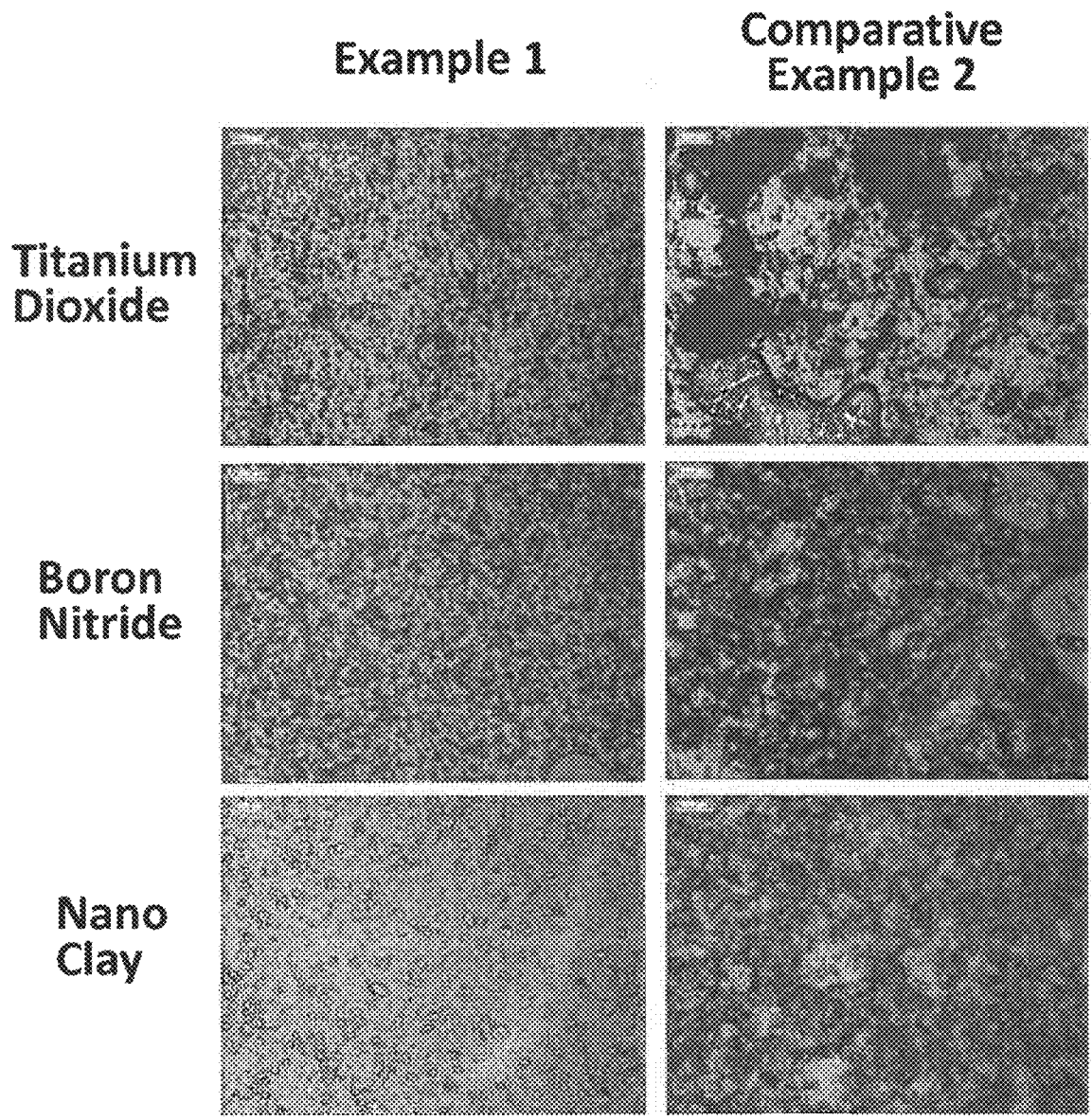
FIG. 1 is a series of microscopy images of blends of Example 1 & Comparative Example 2 gels with Titanium dioxide, Boron nitride & Nano clay.

The inventors herein have unexpectedly discovered a personal care composition which contains an ionically-modified crosslinked silicone network gel in the oil phase of the personal care composition, which network is formed by the hydrosilylation of a hydride-functional silicone with an olefin or a silyl-olefin group, in the presence of a hydrosilylation neutral solvent and a precious metal catalyst, wherein one or more of the hydride-functional silicone, the olefin or the silyl-olefin group, or the hydrosilylation neutral solvent contains an ionic radical moiety, and optionally wherein the ionically-modified crosslinked silicone network is in the absence of polyether moieties and/or polyether crosslinks, and wherein the personal care composition can provide for good sensory benefits, e.g., a silky feel, while also providing the desired degree of wash-off resistance, pigment dispersibility and anti-whitening properties.

As used herein, the expression "ionically-modified crosslinked silicone network composition" can comprise the reaction product of the hydride-functional silicone with the olefin or silyl-olefin group in the optional presence of the solvent and in the presence of the precious metal catalyst and is used interchangeably with the expression "ionically-modified silicone cross-polymer".

It will be understood herein that the "ionically-modified crosslinked silicone network gel" can comprise the ionically-modified crosslinked silicone network that has been sheared in the presence of at least solvent (iv), during and/or after the formation of the ionically-modified crosslinked silicone network.

It will be understood herein that the formation of the ionically-modified crosslinked silicone network can be provided by reaction of a (a) silicone hydride containing two or more silyl-hydride groups, (b) an olefin or silyl-olefin group containing silicone which contains at least two silyl-olefin groups, (c) a silicone containing both at least one, more specifically at least two silyl-hydride group(s) and at least one, more specifically at least two silyl-olefin group(s), (d) a solvent, optionally containing ionic groups, and (e) a catalyst, wherein any one or more of (a), (b), (c), and optionally (d) contains ionic groups as described herein.

Other than in the working examples or where otherwise indicated, all numbers expressing amounts of materials, reaction conditions, time durations, quantified properties of materials, and so forth, stated in the specification and claims are to be understood as being modified in all instances by the term "about" whether or not the term "about" is used in the expression.

It will be understood that any numerical range recited herein includes all sub-ranges within that range and any combination of the various endpoints of such ranges or sub-ranges, be it described in the examples or anywhere else in the specification.

It will also be understood herein that any of the components of the invention herein as they are described by any specific genus or species detailed in the examples section of the specification, can be used in one embodiment to define an alternative respective definition of any endpoint of a range elsewhere described in the specification with regard to that component, and can thus, in one non-limiting embodiment, be used to supplant such a range endpoint, elsewhere described.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

In describing the products of the instant invention as a reaction product of initial materials reference is made to the initial species recited and it is to be noted that additional materials may be added to the initial mixture of synthetic precursors. These additional materials may be reactive or non-reactive. The defining characteristic of the instant invention is that the reaction product is obtained from the reaction of at least the components listed as disclosed. Non-reactive components may be added to the reaction mixture as diluents or to impart additional properties unrelated to the properties of the composition prepared as a reaction product. Thus for example particulate solids such as pigments may be dispersed into the reaction mixture, before during or after reaction to produce a reaction product composition that additionally comprises the non-reactive component, e.g. a pigment. Additional reactive components may also be added; such components may react with the initial reactants or they may react with the reaction product; the phrase "reaction product" is intended to include those possibilities as well as including the addition of non-reactive components.

In one non-limiting embodiment herein the crosslinked ionic silicone network can be in the absence of polyether moieties and/or polyether crosslinks. More specifically, the crosslinked ionic silicone network can be in the absence of one or more moieties selected from glycolide, lactide, butyrolactide and caprolactide. In yet a further non-limiting embodiment herein, the crosslinked ionic silicone network can be in the absence of acrylate and/or olefinic functionality. In yet a further non-limiting embodiment, the crosslinked ionic silicone network is in the absence of olefinic and hydride crosslinking.

It will be understood herein that the expression "oil phase" shall mean that this portion of the personal care composition contains one substantially water-insoluble component, optionally a plurality of substantially water-insoluble components. Here, substantially water-insoluble means that the solubility of the components in water alone or as a mixture is less than 10 g/100 g of water, preferably less than 1 g/100 g of water, particularly preferably less than 0.1 g/100 g of water, measured at 20° C., and the pressure of the ambient atmosphere, i.e. from 900 to 1100 hPa. In the case of the oil phase of the personal care composition according to the invention, the viscosity of the oil phase, measured at 20° C. and a shear gradient of 10 sec$^{-1}$, is from 0.1 to 1,000,000 mPas, preferably from 0.1 to 500,000 mPas, particularly preferably from 0.2 to 100,000 mPas. In the case of the emulsion according to the invention, the oil phase can preferably contain a plurality of components. The individual components may be both substances which are liquid at 20° C. and solids, the total mixture of the individual components having the above-mentioned viscosity. Preferably, but not necessarily, a multicomponent oil phase is a true solution, i.e. a homogeneous phase in which no further phase interfaces occur.

In addition to water, the "aqueous phase" (which is the other of the two phases present in the personal care composition) may contain further components, such as, preferably, acids, bases, salts, water-soluble organic compounds, such as alcohols, carboxylic acids and derivatives thereof, amines or other organic compounds, polymeric or oligomeric compounds, such as polyols or polyamines or polyamidoamines, complex water-soluble organic compounds, such as cosmetic active substances, dyes, organo-element compounds, such as water-soluble organosilicon compounds or water-soluble transition metal compounds. Optionally, the aqueous phase may contain water-wettable particles, such as pigments, fillers or rheological additives.

The expression "shearing" as used herein is understood to mean either the silicone composition may be further processed to adjust the viscosity and sensory feel of the composition. This may be achieved, for example, by subjecting the composition to a moderate to high shearing force. High shear may be applied using, for example, a Sonolator apparatus, a Gaulin Homogenizer or a Micro Fluidizer apparatus and other methods known in the art. Optionally, one or more fluids may be added to the personal care composition prior to the shearing.

It will be understood herein that at rest, the crosslinked ionic silicone network gel exhibits the properties of a solid gel material. The gel of the present invention exhibits high stability and resistance to syneresis, that is, the composition exhibits little or no tendency for fluid to flow from the composition and imparts high stability and syneresis resistance to personal care compositions which include the gel as a component in the oil phase. The high stability and syneresis resistance persists with prolonged aging of such personal care compositions and personal care applications containing such compositions. However, fluid may be released from the network by subjecting the silicone composition to a shearing force, such as, for example, by rubbing the composition between one's fingers, to provide improved sensory feel characteristic of the fluid component of the personal care composition.

In one embodiment herein the personal care composition comprising an oil phase which personal care composition is made by adding an ionically-modified cross-linked silicone network gel to the oil phase of a personal care composition. The ionically-modified cross-linked silicone network gel is made by shearing an ionically-modified cross-linked silicone network. In one embodiment, the ionically-modified crosslinked silicone network comprises the reaction product of (i), (ii), (iii) and (iv) as described herein wherein at least one of (i), (ii) and (iv) is an ionically-modified organosilicone having the general formula (I):

$$M^1_a M^2_b M^3_c D^1_d D^2_e D^3_f T^1_g T^2_h T^3_i Q_j \quad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ where $R^1, R^2, R^3, R^5, R^6, R^8, R^9, R^{10}, R^{11}, R^{13}, R^{15}, R^{16}$ are aliphatic, aromatic or fluoro-containing monovalent hydrocarbon radicals containing from 1 to about 60 carbon atoms, specifically from 1 to about 20 carbon atoms and more specifically from 1 to about 8 carbon atoms, and in some embodiments, the aforestated ranges can have lower limits of 2 or 3 carbon atoms;
where $R^4, R^{12}, R^{17}$ are monovalent or multivalent radical bearing ionic group(s);
where $R^7, R^{14}$ and $R^{18}$ are independently selected from hydrogen, —$OR^{20}$ or unsaturated monovalent hydrocarbon radicals wherein the unsaturated monovalent hydrocarbon radicals contain from 2 to about 60 carbon atoms, more specifically from 2 to about 20 carbon atoms, and most specifically from 2 to about 8 carbon atoms, and wherein each $R^{20}$ is independently selected from hydrogen and monovalent hydrocarbon radicals of from 1 to about 60 carbon atoms, more specifically from 1 to about 20 carbon atoms, and most specifically from 1 to about 8 carbon atoms, and in some embodiments, the aforestated ranges can have lower limits of 2 or 3 carbon atoms;
where the subscripts a, b, c, d, e, f, g, h, i, j are zero or positive subject to the following limitations: the sum a+b+c+d+e+f+g+h+i+j is greater than or equal to 2 and less than or equal to 6000, specifically a+b+c+d+e+f+g+h+i+j is greater than or equal to 2 and less than or equal to 4000, more specifically a+b+c+d+e+f+g+h+i+j is less than or equal to 2000, and in some embodiments, the aforestated ranges can have lower limits of any one of 3, 4, 5, 10, 12, 18, 20, 30 and 50 as well as 100, 200, 300 and 500,
b+e+h is greater than 0, more specifically b+e+h is greater than 1, even more specifically b+e+h is greater than 2, and yet even more specifically b+e+h is from 1 to about 100, further more specifically from 1 to about 50 and most specifically from 1 to about 10, wherein the stated ranges for b+e+h can in some embodiments have lower endpoints of any one of 2, 3, 4, 5, 10, 50 or 100.

In a more specific embodiment, the ionically-modified cross-linked silicone network comprising the ionically modified silicone of formula (I), is such that the monovalent ionic radicals $R^4, R^{12}, R^{17}$ are selected from the formula (II):

$$\text{-A-I}^{x-} \cdot M_n^{y+} \quad (II)$$

where A is a spacing group having selected from a divalent hydrocarbon and hydrocarbonoxy group each containing from 1 to about 60 carbon atoms, more specifically from 1 to about 20 carbon atoms, and most specifically from 1 to about 8 carbon atoms, and in some embodiments, the aforestated ranges can have lower limits of 2 or 3 carbon atoms, wherein the hydrocarbonoxy group contains at least one oxygen heteroatom,
where superscripts x and y are positive integers, such as where x and y are independently from 1 to 6, more specifically from 1 to about 3 subject to the proviso that x is a product of n and y, and each subscript n independently has a value of from 1 to 6, more specifically from about 1 to about 3 where I is an ionic group such as sulfonate —$SO_3^-$, sulfate —$OSO_3^-$, carboxylate —$COO^-$, phosphonate —$PO_3^{2-}$ and phosphate —$OP_3^{2-}$ group, more specifically sulfonate —$SO_3^-$, where M is hydrogen or a cation independently selected from alkali metals, alkaline earth metals, rare earth metals, transition metals, metals, metal complexes, quaternary ammonium, polymeric cations and phosphonium groups.

In another more specific embodiment, the ionically-modified cross-linked silicone network comprising the ionically modified silicone of formula (I), wherein the monovalent radicals $R^4$, $R^{12}$, $R^{17}$ are selected from zwitterions having the formula (III):

$$—R'—NR''_2{}^+—R'''—I \qquad (III)$$

where R' is a divalent hydrocarbon radical containing from 1 to about 60 carbon atoms, specifically from 1 to about 20 carbon atoms, and more specifically from 1 to about 8 carbon atoms and in some embodiments, the aforestated ranges can have lower limits of 2 or 3 carbon atoms, where R" is monovalent hydrocarbon radical containing from 1 to about 60 carbon atoms, specifically from 1 to about 20 carbon atoms and more specifically from 1 to about 8 carbon atoms, and optionally, one or more of a sulfur atom, a nitrogen atom, oxygen atom, and in some embodiments, the aforestated ranges can have lower limits of 2 or 3 carbon atoms, where R'" is divalent hydrocarbon radical containing from 2 to about 20 carbon atoms, specifically from 2 to about 8 carbon atoms and more specifically from 2 to about 4 carbon atoms; and, I is an ionic group such as sulfonate —$SO_3^-$, sulfate —$OSO_3^-$, carboxylate —$COO^-$, phosphonate —$PO_3^{2-}$ group and phosphate —$PO_3^{2-}$ group.

In a more specific embodiment herein there is provided, a personal care composition comprising the ionically-modified cross-linked silicone network gel in the oil phase of the personal care composition, wherein the said cross-linked network of the cross-linked network gel is made by reacting:
(i) a silicone hydride with two or more hydride residues,
(ii) at least one olefinic compound (silicone or non-silicone) with two or more unsaturated radicals,
(iii) an effective amount of precious metal catalyst, and
(iv) optionally, a solvent for swelling the ionically-modified cross-linked silicone network; subject to the limitation that at least (i), (ii) or (iv) comprises the ionically modified silicone of general formula (I).

In a more specific embodiment, the ionically-modified cross-linked silicone network is made by reacting:
(i) an ionically modified silicone hydride bearing at least two Si—H residues and having the general formula (IV):

$$M^1{}_aM^2{}_bM'{}_cD^1{}_dD^2{}_eD'{}_fT^1{}_gT^2{}_hT'{}_iQ_j \qquad (IV)$$

wherein:
$M^1=R^1R^2R^3SiO_{1/2}$
$M^2=R^4R^5R^6SiO_{1/2}$
$M'=R^HR^8R^9SiO_{1/2}$
$D^1=R^{10}R^{11}SiO_{2/2}$
$D^2=R^{12}R^{13}SiO_{2/2}$
$D'=R^HR^{15}SiO_{2/2}$
$T^1=R^{16}SiO_{3/2}$
$T^2=R^{17}SiO_{3/2}$
$T'=R^HSiO_{3/2}$
$Q=SiO_{4/2}$
where $R^H$ is a hydrogen atom;
where $R^1$, $R^2$, $R^3$, $R^5$, $R^6$, $R^8$, $R^9$, $R^{10}$, $R^{11}$, $R^{13}$, $R^{15}$ and $R^{16}$ are as defined above;

where $R^4$, $R^{12}$, $R^{17}$ are each independently monovalent or multi-valent radical bearing ion-pairs,
where the subscripts a, b, c, d, e, f, g, h, i, j are as defined above and b+e+h is greater than 0, and as defined above, and c+f+i>1, more specifically c+f+i≥2 and in some embodiments c+f+i is from about 2 to about 250, more specifically from about 2 to about 100 and most specifically from about 2 to about 25, wherein the ranges of c+f+i stated can have lower endpoints of any one of 3, 4, 5, 10, 50 or 100;
(ii) at least one olefinic compound with two or more unsaturated radicals, more specifically any one of 3, 4, 5, 10, 50 or 100 to about 250 unsaturated radicals;
(iii) an effective amount of precious metal catalyst; and,
(iv) optionally, a solvent for swelling the ionically-modified cross-linked silicone network.

In another more specific embodiment, ionically-modified cross-linked silicone network is made by reacting:
(i) a silicone hydride bearing at least two Si—H residues, more specifically from any one of 3, 4, 5, 10, 50, or 100 hydride groups to about 250 Si—H residues:
(ii) at least one olefin compound containing two or more unsaturated radicals which olefinic compound comprises at least one ionically modified olefinic silicone having the general formula (V):

$$M^1{}_aM^2{}_bM^3{}_cD^1{}_dD^2{}_eD^3{}_fT^1{}_gT^2{}_hT^3{}_iQ_{j'} \qquad (V)$$

wherein:
$M^1=R^1R^2R^3SiO_{1/2}$
$M^2=R^4R^5R^6SiO_{1/2}$
$M^3=R^OR^8R^9SiO_{1/2}$
$D^1=R^{10}R^{11}SiO_{2/2}$
$D^2=R^{12}R^{13}SiO_{2/2}$
$D^3=R^OR^{15}SiO_{2/2}$
$T^1=R^{16}SiO_{3/2}$
$T^2=R^{17}SiO_{3/2}$
$T^3=R^OSiO_{3/2}$
$Q=SiO_{4/2}$
where each $R^O$ is independently selected from an olefinic radical containing from 2 to about 20 carbon atoms, more specifically from about 2 to about 12 carbon atoms and most specifically from about 2 to about 8 carbon atoms, such as the non-limiting examples of vinyl, allyl, acrylate, methacylate; and, an alkyne residue containing monovalent radicals of from 2 to about 20 carbon atoms,
where $R^1$, $R^2$, $R^3$, $R^5$, $R^6$, $R^8$, $R^9$, $R^{10}$, $R^{11}$, $R^{13}$, $R^{15}$ and $R^{16}$ are as defined above;
where $R^4$, $R^{12}$, $R^{17}$ are as defined above;
where the subscripts a', b', c', d', e', f', g', h', i' and j' are zero or positive subject to the following limitations: the sum a'+b'+c'+d'+e'+f'+g'+h'+i'+j' is greater than or equal to 2 and less than or equal to 6000, specifically a'+b'+c'+d'+e'+f'+g'+h'+i'+j' is greater than or equal to 2 and less than or equal to 4000, more specifically
a'+b'+c'+d'+e'+f'+g'+h'+i'+j' is less than or equal to 2000, and in some embodiments, the aforestated ranges can have lower limits of any one of 3, 4, 5, 10, 12, 18, 20, 30 and 50 as well as 100, 200, 300 and 500, and
b'+e'+h' is greater than 0, more specifically b'+e'+h' is greater than 1, even more specifically b'+e'+h' is greater than 2, and yet even more specifically b'+e'+h' is from 1 to about 100, further more specifically from 1 to about 50 and most specifically from 1 to about 25, wherein the stated ranges for b+e+h can in some embodiments have lower endpoints of any one of 2, 3, 4, 5, 10, 50 or 100, and
c'+f'+i'>1, more specifically c'+f'+i'≥2 and in some embodiments c'+f'+i' is from about 2 to about 500, more specifically from about 2 to about 100 and most specifically from about 2 to about 20, wherein the ranges of c'+f'+i' stated can have lower endpoints of any one of 3, 4, 5, 10, 50 or 100;
  (iii) an effective amount of precious metal catalyst; and,
  (iv) optionally, a solvent for swelling the ionically-modified cross-linked silicone network.

In yet another more specific embodiment, the ionically-modified cross-linked silicone network is made by reacting:
  (i) a silicone hydride with at least two Si—H residues, more specifically from any one of 3, 4, 5, 10, 50, or 100 Si—H residues to about 250 Si—H residues;
  (ii) at least one olefinic compound with at least two or more unsaturated radicals, more specifically any one of 3, 4, 5, 10, 50 or 100 to about 250 unsaturated radicals;
  (iii) an effective amount of precious metal catalyst, and
  (iv) a solvent for swelling the ionically-modified cross-linked silicone network comprising an ionically modified silicone copolymer with the general formula (VI):

$$M^7_\alpha M^8_\beta D^7_\chi D^8_\delta T^7_\epsilon T^8_\phi Q_\gamma \qquad (VI)$$

wherein:
  $M^7 = R^1 R^2 R^3 SiO_{1/2}$
  $M^8 = R^4 R^5 R'SiO_{1/2}$
  $D^7 = R^6 R^7 SiO_{2/2}$
  $D^8 = R^8 R'SiO_{2/2}$
  $T^7 = R^9 SiO_{3/2}$
  $T^8 = R'SiO_{3/2}$
  $Q = SiO_{4/2}$,
and wherein, the radicals $R^1$, $R^2$, $R^3$, $R^4$, $R^5$, $R^6$, $R^7$, $R^8$ and $R^9$ are independently selected from aliphatic or aromatic monovalent hydrocarbon radicals having from 1 to 60 carbon atoms, more specifically from 1 to 30 carbon atoms, even more specifically from 1 to 12 carbon atoms and most specifically from 1 to 8 carbon atoms, and optionally each containing at least one hetero atom, such as O, N, S and halogen, and in some embodiments, the aforestated ranges can have lower limits of 2 or 3 carbon atoms,
each $R^1$ is an ion pair,
and the subscripts $\alpha$, $\beta$, $\chi$, $\delta$, $\epsilon$, $\phi$, and $\gamma$ are zero or positive subject to the following limitations: $2 \leq \alpha+\beta+\chi+\delta+\epsilon+\phi+\gamma \leq 6000$, more specifically $2 \leq \alpha+\beta+\chi+\delta+\epsilon+\phi+\gamma \leq 4000$, and most specifically $2 \leq \alpha+\beta+\chi+\delta+\epsilon+\phi+\gamma \leq 2000$ and the aforestated ranges can have lower limits of any one of 3, 4, 5, 10, 12, 18, 20, 30 and 50 as well as 100, 200, 300 and 500; and,
$\beta+\delta+\phi>0$, more specifically, $\beta+\delta+\phi$ is from 1 to about 100, and more specifically, $\beta+\delta+\phi$ is from 1 to about 50, and most specifically $\beta+\delta+\phi$ is from 1 to about 25, wherein said ranges of $\beta+\delta+\phi$ can have in some embodiments, upper limits of any one of 2, 3, 4, 5, 10, 50 or 100.

It will be understood herein that any of the embodiments described herein can be revised accordingly such that the ionically-modified cross-linked silicone network, and personal care compositions containing the same can be formed (and comprise) by combinations of reactants (with the solvent not being a reactant but physically entrained within the reaction product of ionically-modified cross-linked silicone network composition) of any of the following:
  ionic silyl-hydride silicone with non-ionic olefinic compound (silicone or non-silicone) and non-ionic solvent;
  non-ionic silyl-hydride silicone with ionic olefinic compound (silicone or non-silicone) and non-ionic solvent;
  ionic silyl-hydride silicone with ionic olefinic compound (silicone or non-silicone) and non-ionic solvent;
  non-ionic silyl-hydride silicone with non-ionic olefinic compound (silicone or non-silicone) and ionic solvent;
  ionic silyl-hydride silicone with non-ionic olefinic compound (silicone or non-silicone) and ionic solvent;
  non-ionic silyl-hydride silicone with ionic olefinic compound (silicone or non-silicone) and ionic solvent;
  ionic silyl-hydride silicone with ionic olefinic compound (silicone or non-silicone) and ionic solvent;
  ionic functional, silyl-hydride functional and silyl-olefin functional compound with non-ionic solvent; and,
  ionic functional, silyl-hydride functional and silyl-olefin functional compound with ionic solvent.

Hydride-Functional Silicone

In one embodiment herein the at least one hydride-functional silicone has the general formula (IV):

$$M^1_a M^2_b M'_c D^1_d D^2_e D'_f T^1_g T^2_h T'_i Q_j \qquad (IV)$$

which is as defined above and described herein.

As used herein the terminology "hydrocarbon radical" includes acyclic hydrocarbon radicals, alicyclic hydrocarbon radicals and aromatic hydrocarbon radicals.

As used herein in reference to a hydrocarbon radical, the term "monovalent" means that the radical is capable of forming one covalent bond per radical, the term "divalent" means that the radical is capable of forming two covalent bonds per radical and the term "trivalent" means that the radical is capable of forming three covalent bonds per radical. Generally, a monovalent radical can be represented as having been derived from a saturated hydrocarbon compound by conceptual removal of one hydrogen atom from the compound, a divalent radical can be represented as having been derived from a saturated hydrocarbon compound by conceptual removal of two hydrogen atoms from the compound and a trivalent radical can be represented as having been derived from a saturated hydrocarbon compound by conceptual removal of three hydrogen atoms from the compound. For example, an ethyl radical, that is, a —$CH_2CH_3$ radical, is a monovalent radical; a dimethylene radical, that is, a —$(CH_2)_2$— radical, is a divalent radical and an ethanetriyl radical, that is,

radical, is a trivalent radical, each of which can be represented as having been derived by conceptual removal of one or more hydrogen atoms from the saturated hydrocarbon ethane.

As used herein, the terminology "acyclic hydrocarbon radical" means a straight chain or branched hydrocarbon radical, preferably containing from 1 to 60 carbon atoms per radical, which may be saturated or unsaturated and which may be optionally substituted or interrupted with one or more atoms or functional groups, such as, for example, carboxyl, cyano, hydroxy, halo and oxy. As long as these functional groups do not interfere with the cationic cure mechanism of the epoxide or oxirane moiety, suitable monovalent acyclic hydrocarbon radicals may include, for example, alkyl, alkenyl, alkynyl, hydroxyalkyl, cyanoalkyl, carboxyalkyl, alkyloxy, oxaalkyl, alkylcarbonyloxaalkylene, carboxamide and haloalkyl, such as, for example, methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

Suitable divalent acyclic hydrocarbon radicals include, for example, linear or branched alkylene radicals, such as, for example, methylene, dimethylene, trimethylene, decamethylene, ethylethylene, 2-methyltrimethylene, 2,2-dimethyltrimethylene and linear or branched oxalkylene radicals such as, for example, methyleneoxypropylene.

Suitable trivalent acyclic hydrocarbon radicals include, for example, alkanetriyl radicals, such as, for example, 1,1,2-ethanetriyl, 1,2,4-butanetriyl, 1,2,8-octanetriyl, 1,2,4-cyclohexanetriyl and oxaalkanetriyl radicals such as, for example, 1,2,6-triyl-4-oxahexane.

As used herein the term "alkyl" means a saturated straight or branched monovalent hydrocarbon radical. In a preferred embodiment, monovalent alkyl groups are selected from linear or branched alkyl groups containing from 1 to 60 carbons per group, such as, for example, methyl, ethyl, propyl, iso-propyl, n-butyl, iso-butyl, sec-butyl, tert-butyl, pentyl, hexyl, heptyl, decyl, dodecyl.

As used herein the term "alkenyl" means a straight or branched monovalent terminally unsaturated hydrocarbon radical, preferably containing from 2 to 10 carbon atoms per radical, such as, for example, ethenyl, 2-propenyl, 3-butenyl, 5-hexenyl, 7-octenyl and ethenylphenyl.

As used herein, the terminology "alicyclic hydrocarbon radical" means a radical containing one or more saturated hydrocarbon rings, specifically containing from 4 to 12 carbon atoms per ring, per radical which may optionally be substituted on one or more of the rings with one or more alkyl radicals, each preferably containing from 2 to 6 carbon atoms per alkyl radical, halo radicals or other functional groups and which, in the case of a monovalent alicyclic hydrocarbon radical containing two or more rings, may be fused rings. Suitable monovalent alicyclic hydrocarbon radicals include, for example, cyclohexyl and cyclooctyl. Suitable divalent hydrocarbon radicals include, saturated or unsaturated divalent monocyclic hydrocarbon radicals, such as, for example, 1,4-cyclohexylene. Suitable trivalent alicyclic hydrocarbon radicals include, for example, cycloalkanetriyl radicals such as, for example, 1-dimethylene-2,4-cyclohexylene, 1-methylethylene-3-methyl-3,4-cyclohexylene.

As used herein, the terminology "aromatic hydrocarbon radical" means a hydrocarbon radical containing one or more aromatic rings per radical, which may, optionally, be substituted on the aromatic rings with one or more alkyl radicals, each preferably containing from 2 to 6 carbon atoms per alkyl radical, halo radicals or other functional groups and which, in the case of a monovalent aromatic hydrocarbon radical containing two or more rings, may be fused rings. Suitable monovalent aromatic hydrocarbon radicals include, for example, phenyl, tolyl, 2,4,6-trimethylphenyl, 1,2-isopropylmethylphenyl, 1-pentalenyl, naphthyl, anthryl, eugenol and allylphenol as well as aralkyl radicals such as, for example, 2-phenylethyl. Suitable divalent aromatic hydrocarbon radicals include, for example, divalent monocyclic arenes such as, for example, 1,2-phenylene, 1,4-phenylene, 4-methyl-1,2-phenylene, phenylmethylene. Suitable trivalent aromatic hydrocarbon radicals include, for example, trivalent monocyclic arenes such as, for example, 1-trimethylene-3,5-phenylene.

In one non-limiting embodiment herein, $R^1$, $R^2$, $R^3$, $R^5$, $R^6$, $R^8$, $R^9$, $R^{10}$, $R^{11}$, $R^{13}$, $R^{15}$ and $R^{16}$ are independently as described herein, and optionally wherein each can contain at least one heteroatom selected from the group consisting of oxygen and halogen.

Some specific non-limiting examples of hydrocarbon radicals that may be used herein, such as in the non-limiting example of the hydrocarbon radicals used for $R^1$, $R^2$, $R^3$, $R^5$, $R^6$, $R^8$, $R^9$, $R^{10}$, $R^{11}$, $R^{13}$, $R^{15}$ and $R^{16}$ that may be suitable are methyl, ethyl, n-propyl, iso-propyl, n-butyl, isobutyl, tert-butyl, n-pentyl, iso-pentyl, neopentyl and tert-pentyl; hexyl, such as the n-hexyl group; heptyl, such as the n-heptyl group; octyl, such as the n-octyl and isooctyl groups and the 2,2,4-trimethylpentyl group; nonyl, such as the n-nonyl group; decyl, such as the n-decyl group; cycloalkyl radicals, such as cyclopentyl, cyclohexyl, cycloheptyl radicals and methylcyclohexyl radicals. Some specific non-limiting examples of aryl hydrocarbon radicals that may be suitable are phenyl, napthyl; o-, m- and p-tolyl, xylyl, ethylphenyl and benzyl.

In one embodiment herein $R^I$, is independently a monovalent hydrocarbon radical bearing ion-pairs and having the general formula (II) as described herein.

   (II)

In one specific embodiment herein, A is a divalent arylene group selected from the group consisting of:
—$(CH_2)_l C_6H_4(CH_2)_k$—,
—$CH_2CH(CH_3)(CH_2)_k C_6H_4$— and,
—$CH_2CH(R^{13*})(CH_2)_l C_6H_3R''$—
where $R^{13*}$ is a monovalent hydrocarbon radical having from one to sixty carbon atoms, more specifically, from one to 30 carbon atoms, even more specifically from 1 to 12 carbon atoms and most specifically from 1 to 6 carbon atoms;
where l has a value of 0 to 20, more specifically from 1 to 10 and k has a value of 0 to 20, specifically from 0 to 10.

In another specific embodiment herein, A is a divalent alkylene group of the formula —$(CHR^{14*})_m$— where m has a value of from 1 to 20, specifically from 1 to about 10 and $R^{14*}$ is hydrogen or a monovalent hydrocarbon radical having from one to sixty carbon atoms, more specifically, from one to 30 carbon atoms, even more specifically from 1 to 12 carbon atoms and most specifically from 1 to 6 carbon atoms.

In yet another specific embodiment herein, A is selected from the group consisting of —$CH_2CH_2CH_2$—, —$CH_2CH(CH_3)$—, —$CH_2CH(CH_3)CH_2$—, and —$CH_2CH_2CH(CH_2CH_3)CH_2CH_2CH_2$—.

In yet even another specific embodiment herein A is of the formula:

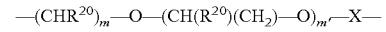

wherein m has a value of from 2 to 50, more specifically from 2 to about 10 and m' has a value of from 1 to 50, more specifically from 1 to about 25 and $R^{20}$ is hydrogen or a monovalent hydrocarbon radical having from one to sixty carbon atoms, more specifically, from one to 30 carbon atoms, even more specifically from 1 to 12 carbon atoms and most specifically from 1 to 6 carbon atoms and X is null or a divalent hydrocarbon radical optionally containing at least one heteroatom, such as the non-limiting examples of O, N, S or halogen.

In one embodiment herein, M can be a cation independently selected from univalent and polyvalent forms of Li, Na, K, Cs, Mg, Ca, Ba, Zn, Cu, Fe, Ni, Ga, Al, Mn, Cr, Ag, Au, Pt, Pd, Pb, Sb, Ru, Sn and Rh, such as the non-limiting examples of $Mn^{+2}$ and $Mn^{+3}$.

In one non-limiting embodiment herein M can specifically be a cation selected from univalent and polyvalent forms of Na, K, Mg, Ca, Zn, Cu, Fe, Ni, Co and Al.

In another specific non-limiting embodiment herein the stoichiometric subscripts a, b, c, d, e, f, g, h, i, j, a', b', c', d', e', f', g', h', i', j' and α, β, χ, δ, ε, φ, γ (as described herein) are either zero or positive subject to the limitations 2≤a+b+c+d+e+f+g+h+i+j≤4000, 2≤a'+b'+c'+d'+e'+f'+g'+h'+i'+j'≤4000 and, 2≤α+β+χ+δ+ε+φ+γ≤4000; and, more specifically, $2 \geq a+b+c+d+e+f+g+h+i+j \leq 2000$, $2 \geq a'+b'+c'+d'+e'+f'+g'+h'+i'+j' \leq 2000$ and, $2 \leq \alpha+\beta+\chi+\delta+\epsilon+\phi+\gamma \leq 2000$. In one specific embodiment herein these values the aforementioned stoichiometric subscripts ranges can also have a lower endpoint value of any one of 3, 4, 5, 10, 12, 18, 20, 30 and 50 as well as 100, 200, 300 and 500.

In one specific non-limiting embodiment herein the subscripts b, e, h and b', e', h' are zero or positive, subject to the limitations that $b+e+h>0$ and $b'+e'+h'>0$, more specifically, $b+e+h>1$ and $b'+e'+h'>1$, and even more specifically, $b+e+h>2$ and $b'+e'+h'>2$.

In another specific non-limiting embodiment herein the subscripts b, e, h and b', e', h' are zero or positive, subject to the limitations that $b+e+h>0$ or $b'+e'+h'>0$, more specifically, $b+e+h>1$ or $b'+e'+h'>1$, and even more specifically, $b+e+h>2$ or $b'+e'+h'>2$.

In yet another specific non-limiting embodiment herein, the subscripts, b, e, h, b', e', h', and $\beta$, $\delta$ and $\phi$, are either zero or positive, subject to the limitations that $b+e+h+b'+e'+h'=0$ and $\beta+\delta+\phi>0$, more specifically, $b+e+h+b'+e'+h'=0$ and $\beta+\delta+\phi>1$ and most specifically, $b+e+h+b'+e'+h'=0$ and $\beta+\delta+\phi>2$.

It will be understood herein that the setting apart of the specification into portions such as silicon-hydride, olefin, solvent, catalyst, personal care composition and processes thereto are only for means of ease to the reader and are not limiting in any aspect as to the various descriptive support provided in the respective sections, and such descriptive support applies equally and interchangeably to all portions of the specification. Thus, it is understood herein that the respective R definitions, subscript values and other variables defined herein with regard to one section, such as for example, the silicon-hydride can have the same definitions with regard to the description section relating to the olefin, the solvent and the catalyst, as well as the process embodiments herein, and also in any other way these variables have been described elsewhere in the composition or process embodiments described herein, and vice-versa.

Olefin

In one embodiment herein the at least one olefinic compound with two or more unsaturated radicals or silyl-olefin group containing silicone which contains at least two silyl-olefin groups is selected from the group consisting of at least one of non-silicone olefin and organo-modified silicone olefin, wherein the organo-modified silicone olefin has the general structure (V) as described herein.

In another more specific embodiment, the at least one olefin can comprise a combination of a non-silicone olefin such as the non-limiting example of an α,ω-diene, and an organo-modified silicone olefin of the general structure (V) as described herein:

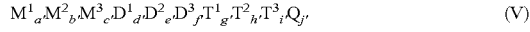

In one embodiment herein, some non-limiting examples of α,ω-diene include butadiene, hexadiene, octadiene, norbornene, ethylidene norbornene, vinylnorbornene, norbornadiene, and dicyclopentadiene and combinations thereof.

In yet another more specific embodiment, the at least one olefin comprises a blend of at least one multifunctional olefin and a mono-functional olefin.

In another more specific embodiment herein $R^O$ is a monovalent olefin radical having the structure (VII):

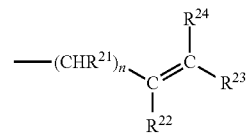

where $R^{21}$, $R^{22}$, $R^{23}$ and $R^{24}$ are each independently selected from the group of hydrogen and monovalent hydrocarbon radicals containing from 1 to 60 carbon atoms, more specifically 1 to 30 carbon atoms, even more specifically from 1 to 12 carbon atoms and most specifically from 1 to about 6 carbon atoms.

Solvent

In one non-limiting embodiment herein, if the hydride-functional silicone and the olefin do not bear any ionic group, the solvent can comprise the ionic moieties present in the ionically-modified silicone cross-polymer.

In one non-limiting embodiment herein the solvent comprises an ionically-modified silicone polymer having the general structure (VI) as described herein:

and the subscripts α, β, χ, δ, ε, φ, and γ are zero or positive subject to the following limitations: $2 \leq \alpha+\beta+\chi+\delta+\epsilon+\phi+\gamma \leq 6000$; and, $\beta+\delta+\phi>0$.

In another embodiment herein, solvents which are suitable for use are those compounds or mixtures of two or more compounds that are in a liquid state at or near room temperature, e.g., 20° C. to about 50° C. and about one atmosphere pressure, and include such non-limiting examples as those selected from silicone fluids, hydrocarbon fluids, esters, alcohols, fatty alcohols, glycols, organic waxes and organic oils.

In one embodiment herein the solvent can comprise a blend of two or more solvents.

In yet another embodiment, the silicone fluids may be selected from the group consisting of low viscosity silicone fluids and volatile silicone fluids.

In yet even another embodiment herein, the solvent is at least one selected from the group consisting of isodecane, isohexadecane, hydrogenated polyisobutene, jojoba, cylcopentasiloxane, dimethicone, bis-phenylpropyl dimethicone, octyldodecyl neopentanoate, oleyl oleate, oleyl alcohol and isomyristyl alcohol.

In another embodiment the carrier solvent is a cyclic silicone fluid of the general formula $D_r$, where $D=R^{15}R^{16}SiO_{2/2}$ and where $R^{15}$ and $R^{16}$ are monovalent hydrocarbon radicals of from 1 to 6 carbon atoms, more specifically methyl, and r is an integer of from 3 to 12, more specifically, from 4 to 8. Specifically, the cyclic silicone fluid can be selected from hexamethylcyclotrisiloxane, octamethylcyclotetrasiloxane, decamethylcyclopentasiloxane and dodecamethylcyclohexasiloxane.

In one embodiment, the solvent of the present invention can comprise an emollient compound. Suitable emollient compound include any fluid that provides emollient properties, that is, that when applied to skin, tend to remain on the surface of the skin or in the stratum corneum layer of the skin to act as lubricants, reduce flaking and to improve the appearance of the skin. Emollient compound are generically known and include, for example, hydrocarbons, such as for example, isododecane, isohexadecane and hydrogenated polyisobutene, organic waxes, such as for example, jojoba, silicone fluids, such as, for example, cyclopentasiloxane, dimethicone and bis-phenylpropyl dimethicone, esters, such as, for example, octyldodecyl neopentanoate and oleyl oleate, as well as fatty acids and alcohols, such as for example, oleyl alcohol and isomyristyl alcohol.

In one non-limiting embodiment herein the ionically-modified silicone crosspolymer is swellable by the solvent.

In another embodiment herein the solvent is a hydrophilic emollient selected from the group consisting of glycerine, sorbitol, aqueous solution of moisturizing additives and combinations thereof.

In one specific embodiment the solvent is selected from silicone oil, an organic oil and combinations thereof.

Because it is possible to vary the compositional parameters of the ionically-modified silicone cross-polymer composition of the invention in an almost limitless fashion, by varying the compositional parameters of the ionically-modified silicone cross-polymer, some compositions herein are both water swellable and oil swellable while others are only water swellable or oil swellable. The amount of crosslinking present in the ionically-modified silicone cross-polymer may be characterized with respect to the degree of swelling exhibited by the cross-polymer in the solvent. In another embodiment, the crosslinked structure of the ionically-modified silicone cross-polymer is effective to allow the ionically-modified silicone cross-polymer to be swollen from its original volume to a swollen volume that is a factor of from 1.01 to 5000, more preferably from 2 to 1000, and even more preferably from 5 to 500, times its original volume. The original volume of the ionically-modified silicone cross-polymer can be determined, for example, by extracting or evaporating all of the solvent component from the personal care composition of the present invention to leave the original volume, that is, the volume of the ionically-modified silicone cross-polymer in the absence of the fluid.

In a more specific embodiment, the personal care composition of the present invention comprises, per 100 parts by weight ("pbw") of the ionically-modified silicone cross-polymer, from 1 pbw to 99.9 pbw, more preferably from 70 pbw to 99.5 pbw, and still more preferably from 85 pbw to 99 pbw of the solvent.

Precious-Metal Catalyst

Many types of precious metal catalysts, e.g., platinum catalysts are known and such platinum catalysts may be used for the hydrosilylation reaction in the present invention. When optical clarity is required the preferred platinum catalysts are those platinum compound catalysts that are soluble in the reaction mixture. The platinum compound can be selected from those having the formula (PtCl$_2$Olefin) and H(PtCl$_3$Olefin) as described in U.S. Pat. No. 3,159,601, hereby incorporated by reference. A further platinum containing material usable in the compositions of the present invention is the cyclopropane complex of platinum chloride described in U.S. Pat. No. 3,159,662 hereby incorporated by reference. Further the platinum containing material can be a complex formed from chloroplatinic acid with up to 2 moles per gram of platinum of a member selected from the class consisting of alcohols, ethers, aldehydes and mixtures of the above as described in U.S. Pat. No. 3,220,972 hereby incorporated by reference. The catalysts most specifically used herein are described in U.S. Pat. Nos. 3,715,334; 3,775,452; and 3,814,730 to Karstedt. Additional background concerning the art may be found at J. L. Spier, "Homogeneous Catalysis of Hydrosilation by Transition Metals, in Advances in Organometallic Chemistry, volume 17, pages 407 through 447, F. G. A. Stone and R. West editors, published by the Academic Press (New York, 1979).

In one embodiment the precious metal catalysts that may be used herein, are such as the non-limiting examples of rhodium, ruthenium, palladium, osmium, iridium and platinum catalysts and combinations thereof.

In one embodiment herein the platinum catalyst is in a soluble complex form.

In one other embodiment, the platinum catalyst is selected from the group consisting of platinic chloride, chloroplatinic acid, bis(acetylacetonato)platinum, ($\eta^5$-Cyclopentadienyl)trialkylplatinum and combinations thereof.

Persons skilled in the art can easily determine an effective amount of precious metal catalyst. The catalyst can be present in a very wide range, but normally a range of from between 0.1 and 10,000 ppm, more specifically from between 1 and 100 ppm. In one embodiment herein the basis amount of the catalyst is based on the amount of ionically-modified silicone cross-polymer or the amounts of the respective components used to produce the ionically-modified silicone cross-polymer.

Personal Care Composition

In one embodiment herein, the personal care compositions of the present invention are self-emulsifying.

In another embodiment herein, the silicone network described herein may be further processed under low to high shear to adjust the viscosity and sensory feel of the composition and to provide for the silicone network gel as described herein. This may be achieved, for example, by subjecting the composition to a moderate to high shearing force. High shear may be applied using, for example, a Sonolator apparatus, a Gaulin Homogenizer or a Micro Fluidizer apparatus. Optionally, one or more carrier solvent may be added to the silicone network composition prior to the shearing.

In a specific embodiment, the personal care composition of the present invention is a solid, typically having a creamy consistency, wherein the ionically-modified silicone cross-polymer acts as a means for gelling the fluid to reversibly impart characteristics of a solid to the fluid. At rest, the ionicially-modified silicone network gel exhibits the properties of a solid gel material. The ionicially-modified silicone network gel of the present invention exhibits high stability and resistance to syneresis, that is, the gel exhibits little or no tendency for fluid to flow from the gel and imparts high stability and syneresis resistance to the oil phase of personal care compositions which include the ionically-modified silicone cross-polymer as a component therein. The high stability and syneresis resistance persists with prolonged aging of such ionicially-modified silicone cross-polymer gel and the oil phase of personal care compositions containing the ionicially-modified silicone network gel. However, solvent may be released from the ionicially-modified silicone cross-polymer gel by subjecting the personal care composition to a shearing force, such as, for example, by rubbing the composition between one's fingers, to provide improved sensory feel characteristic of the fluid component of the crosslinked silicone network material.

Water (or a water equivalent such as a non-aqueous hydroxylic solvent), siloxane, linear or cyclic, or lipophilic fluid (oil swelling agent, oil swellable) may be used as the solvent which may function as a swelling agent for the crosslinked ionic silicone network. Lipophilic fluids suitable for use as the solvent component of the personal care composition of the present invention are those described herein. In a preferred embodiment, the solvent component of the composition of the present invention exhibits a viscosity of below about 1,000 cSt, preferably below about 500 cSt, more preferably below about 250 cSt, and most preferably below 100 cSt, at 25° C.

In one preferred embodiment, the cross-polymer is an ionically-modified silicone cross-polymer that is insoluble in various fluid components, but that is capable of being swollen by the solvent. The amount of crosslinking present in the ionically-modified silicone cross-polymer may be characterized with respect to the degree of swelling exhibited by the cross-polymer in the solvent.

In another specific embodiment, the cross linked structure of the ionically-modified silicone cross-polymer is effective to allow the cross-polymer to be swollen by a low molecular weight silicone fluid, such as, for example, decamethylcyclopentasiloxane, from its original volume to a swollen volume as stated above.

The ionically-modified silicone cross-polymer of the present invention may be utilized as prepared or as the silicone gel component in personal care compositions such as personal care emulsions. As is generally known, emulsions comprise at least two immiscible phases one of which is continuous and the other which is discontinuous. In one embodiment herein, the non-miscible phases (immiscible phases) can be selected from the group consisting of aqueous, non-aqueous, and solid particulates.

Further emulsions may be liquids with varying viscosities or solids. Additionally, the particle size of the emulsions may render them microemulsions, and when sufficiently small, microemulsions may be transparent. Further it is also possible to prepare emulsions of emulsions and these are generally known as multiple emulsions. These emulsions may be: 1) aqueous emulsions where the discontinuous phase comprises water and the continuous phase comprises the cross linked ionic silicone network (or gel thereof) of the present invention; 2) aqueous emulsions where the discontinuous phase comprises the ionically-modified silicone cross-polymer (or gel thereof) of the present invention and the continuous phase comprises water; 3) non-aqueous emulsions where the discontinuous phase comprises a non-aqueous hydroxylic solvent and the continuous phase comprises the ionically-modified silicone cross-polymer (or gel thereof) of the present invention; and 4) non-aqueous emulsions where the continuous phase comprises a non-aqueous hydroxylic organic solvent and the discontinuous phase comprises the ionically-modified silicone cross-polymer (or gel thereof) of the present invention.

In one embodiment herein, the ionically-modified silicone cross-polymer is compatible with a particulate additive. In another more specific embodiment, the particulate additive is selected from inorganic particulates, polymeric latexes, and pigments.

As used herein the term "non-aqueous hydroxylic organic compound" or "non-aqueous hydroxylic solvent" means hydroxyl containing organic compounds exemplified by alcohols, glycols, polyhydric alcohols and polymeric glycols and mixtures thereof that are liquid at room temperature, e.g. about 25° C., and about one atmosphere pressure, and are used interchangeably with the term "solvent" as the same component. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, isopropyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Once the desired form is attained whether as a silicone only phase, an anhydrous mixture comprising the silicone phase, a hydrous mixture comprising the silicone phase, a water-in-oil emulsion, an oil-in-water emulsion, or either of the two non-aqueous emulsions or variations thereon, the resulting material is usually a high viscosity cream with good feel characteristics, and high absorbance of volatile siloxanes. It is capable of being blended into personal care formulations (for example into the oil phase of a personal care composition) for hair care, skin care, and the like. In one embodiment herein, the crosslinked ionic silicone network can bind and slow release cosmetic actives.

In one embodiment the personal care composition can be a personal care application selected from the group consisting of deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nail creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a more specific embodiment, the personal care composition of the present invention further comprises one or more personal care ingredients. Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

Suitable personal care compositions are made by combining, in a manner known in the art, such as, for example, by mixing, one or more of the above components with ionically-modified silicone cross-polymer (or gel thereof).

Suitable personal care compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions; such as is described above.

In one useful embodiment, an antiperspirant composition comprises the ionically-modified silicone cross-polymer composition of the present invention and one or more active antiperspirant agents. Suitable antiperspirant agents include, for example, the Category I active antiperspirant ingredients listed in the U.S. Food and Drug Administration's Oct. 10, 1993 Monograph on antiperspirant drug products for overthe-counter human use, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, aluminum zirconium glycine complexes, such as, for example, aluminum zirconium tetrachlorohydrex gly.

In another useful embodiment, a skin care composition comprises the ionically-modified silicone cross-polymer, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoylmethane, p-aminobenzoic acid and octyl dimethyl-p-aminobenzoic acid.

In another useful embodiment, a color cosmetic composition, such as, for example, a lipstick, a makeup or a mascara composition comprises the crosslinked ionic silicone network, and a coloring agent, such as a pigment, a water soluble dye or a liposoluble dye.

In another useful embodiment, the personal care compositions of the present invention are utilized in conjunction with fragrant materials. These fragrant materials may be fragrant compounds, encapsulated fragrant compounds or fragrance releasing compounds that either the neat compounds or are encapsulated.

Process of Preparing Ionically-Modified Silicone Cross-Polymer

As stated above, there is provided herein a process of preparing a personal care composition comprising an oil phase which process comprises adding an ionically-modified crosslinked silicone network gel to the oil phase of a personal care composition wherein the ionically-modified silicone network gel is made by the process comprising reacting:

(i) a silicone hydride with at least two Si—H residues,
(ii) at least one olefinic compound (silicone or non-silicone) with two or more unsaturated radicals,
(iii) an effective amount of precious metal catalyst, and
(iv) optionally, a solvent for swelling the crosslinked silicone network; subject to the limitation that at least (i), (ii) or (iv) is selected from the ionically modified silicone of general formula (I) as described herein:

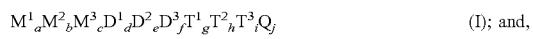

$$M^1_a M^2_b M^3_c D^1_d D^2_e D^3_f T^1_g T^2_h T^3_i Q_j \quad \text{(I); and,}$$

shearing the ionically-modified cross-linked silicone network using at least a solvent (iv) to provide the ionically-modified cross-linked silicone network gel.

In one embodiment herein the amount of ionically-modified crosslinked silicone network is based on the total weight of the personal care composition which contains a ionically-modified crosslinked silicone network which is formed by the reaction of components described herein. In one non-limiting embodiment, this amount is of from about 1 parts by weight to about 99 parts by weight, more specifically from about 5 parts by weight to 50 parts by weight, more specifically from about 10 parts by weight to about 40. Such amounts can be used as the amount of the ionically-modified crosslinked silicone network gel in the oil phase of the personal care composition.

It will be understood herein that the ionically-modified silicone cross-polymer gel for use in the oil phase of personal care composition and applications, such as the gel made by the process(es) described herein, can be such that there are no polyether substituent moieties in the ionically-modified silicone cross-polymer used to make the gel.

In one embodiment, the amounts of hydride-functional silicone (i) and olefin (ii) that is employed in the process(es) described herein can be present in any amount that provides for a molar equivalent amount of silicon-hydride moieties to the molar amount of unsaturated moieties present in the olefin (ii). In one non-limiting embodiment, either the molar amount of silicon-hydride moieties present in the hydride-functional silicone (i) exceed the molar amount of unsaturated moieties present in the olefin (ii) or vice-versa, the molar amount of unsaturated moieties present in the olefin (ii) exceed the molar amount of silicon-hydride moieties present in the hydride-functional silicone (i). In a more specific embodiment the amount of hydride-functional silicone (i) that is employed in the process(es) described herein can be present in any equivalent amount that provides for a molar ratio of silicon-hydride moieties in silicone (i) to unsaturated moieties in olefin (ii) of from 1:100 to about 100:1, more specifically from about 1:10 to about 10:1.

In one embodiment herein, the amount of solvent (iv) that can be employed in the process(es) and compositions described herein comprise from about 0 weight percent to about 99.9 weight percent, more specifically from about 0 weight percent to about 99 weight percent and most specifically from about 0 weight percent to about 95 weight percent, said weight percents being based on the total weight of the ionically-modified silicone cross-polymer composition for personal care applications. In one embodiment herein the lower endpoint of the aforementioned ranges can be any one of 0.1 weight percent, 0.5 weight percent, 1 weight percent, 5 weight percent and 10 weight percent.

In one specific embodiment herein the reacting and shearing steps of the process(es) described herein can be conducted at a temperature of from about 0° C. to about 200° C., more specifically, from about 10° C. to about 150° C. and most specifically from about from about 20° C. to about 120° C., and at a pressure of from about 0.1 atm to about 10 atm, more specifically of from about 0.5 atm to about 5 atm and most specifically of from about 0.9 atm to about 2 atm.

In one specific embodiment herein the step (b) of the process(es) and steps thereof which are described herein can be conducted for a period of from about 5 minutes to about 48 hours, more specifically from about 20 minutes to about 36 hours and most specifically from about 1 hour to about 12 hours.

In one embodiment the process of preparing an ionically-modified silicone cross-polymer gel for use in the oil phase of personal care compositions can further comprise the use of a hydrosilylation inhibitor, such as the non-limiting example of mercaptyl compounds. In one embodiment the inhibitor can be used during the shearing step of the process of preparing an ionically-modified silicone cross-polymer gel for personal care compositions. Non-limiting examples of hydrosilylation inhibitors are described in U.S. Pat. Nos. 3,445,420, 4,256,870, 4,465,818, 4,562,096, and 5,629,387, the disclosures of which are hereby incorporated by reference. It is well within the skill in the art to select a suitable hydrosilylation inhibitor.

It will be understood herein that the respective R values, subscripts and other variables defined herein can have the same definitions in the process embodiments herein as these variables have in the composition embodiments described herein and vice-versa, and furthermore, the values of these variables can have the same definitions in the various different embodiments described herein and can be used interchangeably throughout any of the embodiments described herein.

In one embodiment herein that the reaction of hydride-functional silicone (i) with olefin (ii) can be conducted under general hydrosilylation conditions which can comprises the use of an effective amount of precious metal catalyst (iii) such as those catalysts described herein, e.g., a platinum catalyst, and in the amounts described herein, and in the presence of a solvent (iv) and in conditions as described herein and/or as are known to those skilled in the art.

In one embodiment herein, it is to be noted that acetylene analogs of the olefin (ii) will react to form similar products. Thus, as used herein, the phrase an "olefinic compound selected from non-silicone olefin and an organo-modified silicone olefin of the general structure (V)", is intended to also include an acetylenically unsaturated molecule. The phrase "an acetylenically unsaturated molecule" means a molecule possessing one or more interior, pendant or terminal carbon to carbon triple bonds, i.e. a —C≡C— linkage.

The ionic silicon hydride (i) and olefinic (ii) functionalities can be made by a variety of techniques that are known in the art, such as those described in U.S. Pat. No. 8,697,829, the contents of which are incorporated by reference herein.

The non-ionic silicone olefins (ii) can be made by a variety of techniques that are known in the art. They are typically prepared by equilibration reactions of suitable monomers catalyzed by acids or bases.

The solvent (iv) when it is of the general formula (VI) can be made by a variety of techniques that are known in the art, such as those described in JP 6,247,827 and JP 6,247,835, the contents of which are incorporated by reference herein.

EXAMPLES

The following examples exemplify, but do not limit, the present invention. The storage modulus was measured at 350 μm, 25° C. temperature, 1 Hz frequency, and 1% strain.

Example 1

0.21 parts by weight of C-30 alpha olefin (from Chevron Phillips Company), 48.78 parts by weight vinyl end capped polydimethyl-co-methyl-2-methylpropylphenylsulfonate siloxane with 0.062 mmol·g−1 vinyl and 0.328 mmol·g−1 sulfonate, and 150 parts by weight of decamethylpentacyclosiloxane were placed in a Ross mixture. The mixture was stirred, and heated to 80° C. till C-30 alpha olefin dissolved completely. Subsequently, the mixture was cooled down to 35° C., 1.02 parts by weight of a silanic hydrogen fluid represented by the average composition formula: $(CH_3)_3SiO((CH_3)_2SiO)_{20}((CH_3)HiSiO)_{10}Si(CH_3)_3$ and 0.10 parts by weight of a Karstedt's catalyst containing 2% Platinum metal were added thereto and stirred till uniform mixture was obtained. Then, the mixture was stirred at 35° C. for 15 minutes to facilitate hydrosilylation giving solid cross-linked material, mixing was continued for another 45 minutes. Temperature was ramped to 80° C. and the solid material was mixed for 2 hours to ensure complete cross-linking/hydrosilylation. The solid polymer content of the cross linked material was found to be between 24-26%. The storage modulus G' of the cross linked material was 4400 Pa. 20 parts by weight of the above described cross-linked material containing 25% solid was blended with 80 parts by weight of decamethylpentacyclosiloxane in a Silverson mixer for 5 minutes at 5000 rpm. The material obtained was additionally subjected to a 5 minute blending cycle at 5000 rpm 4 times. The swelled material was then passed through a Microfluidizer three times to get a smooth, silky gel containing ~5% solid-viscosity 6,600 cps. The storage modulus G' of the cross linked material was 80 Pa.

Example 2

35 parts by weight of cross-linked material containing 25% solid as described in Example 1 was blended with 65 parts by weight of decamethylpentacyclosiloxane in a Silverson mixer for 5 minutes at 5000 rpm. The material obtained was additionally subjected to a 5 minute blending cycle at 5000 rpm 4 times. The swelled material was then passed through a Microfluidizer three times to get a smooth, silky, cushioning gel containing ~8.5% solid-viscosity 30,000 cps. The storage modulus G' of the cross linked material was 1400 Pa.

Example 3

0.11 parts by weight of C-30 alpha olefin (from Chevron Phillips Company), 24.40 parts by weight vinyl end capped polydimethyl-co-methyl-2-methylpropylphenylsulfonate siloxane with 0.062 mmol·g−1 vinyl and 0.328 mmol·g−1 sulfonate, and 74.5 parts by weight of decamethylpentacyclosiloxane were placed in a Ross mixer. The mixture was stirred, and heated to 80° C. till the C-30 alpha olefin dissolved completely. Subsequently, the mixture was cooled down to 35° C., 0.24 parts by weight of an MHQ-9 resin hydride available from Momentive Performance Materials with 0.93% hydride and 0.05 parts by weight of a Karstedt's catalyst containing 2% Platinum metal were added thereto and stirred till uniform mixture was obtained. Then, the mixture was stirred at 35° C. for 15 minutes to facilitate hydrosilylation giving solid cross-linked material, mixing was continued for another 45 minutes. The temperature was ramped to 80° C. and the solid material was mixed for 2 hours to ensure complete cross-linking/hydrosilylation. The solid polymer content of the cross linked material was found to be between 24-26%.

Example 4

0.21 parts by weight of C-30 alpha olefin (from Chevron Phillips Company), 48.78 parts by weight vinyl end capped polydimethyl-co-methyl-2-methylpropylphenylsulfonate siloxane with 0.062 mmol·g$^{-1}$ vinyl and 0.328 mmol·g$^{-1}$ sulfonate, and 150 parts by weight of 5 cps polydimethylsiloxane available from Momentive Performance Materials were placed in a Ross mixer. The mixture was stirred, and heated to 80° C. till the C-30 alpha olefin dissolved completely. Subsequently, the mixture was cooled down to 35° C., 1.02 parts by weight of a silanic hydrogen fluid represented by the average composition formula: $(CH_3)_3SiO((CH_3)_2SiO)_{20}((CH_3)HSiO)_{10}Si(CH_3)_3$ and 0.10 parts by weight of a Karstedt's catalyst containing 2% Platinum metal were added thereto and stirred till a uniform mixture was obtained. Then, the mixture was stirred at 35° C. for 15 minutes to facilitate hydrosilylation giving a solid cross-linked material, mixing was continued for another 45 minutes. The temperature was ramped to 80° C. and the solid material was mixed for 2 hours to ensure complete crosslinking/hydrosilylation. The solid polymer content of the cross linked material was found to be between 24-26%.

Example 5

90 parts by weight of cross-linked material of Example 4 was blended with 110 parts by weight of 5 cps polydimethylsiloxane available from Momentive Performance Materials in a Silverson mixer for 5 minutes at 5000 rpm. The material obtained was additionally subjected to a 5 minute blending cycle at 5000 rpm 4 times. The swelled material was then passed through a Microfluidizer three times to get a smooth, silky, cushioning gel containing 11.25% solid.

Example 6

90 parts by weight of the cross-linked material of Example 4 was blended with 110 parts by weight of Silsoft 034 (available from Momentive Performance Materials) in a Silverson mixer for 5 minutes at 5000 rpm. The material obtained was additionally subjected to a 5 minute blending cycle at 5000 rpm 4 times. The swelled material was then passed through a Microfluidizer three times to get a smooth, silky, cushioning gel containing 11.25% solid.

Example 7

0.21 parts by weight of C-30 alpha olefin (from Chevron Phillips Company), 48.78 parts by weight vinyl end capped polydimethyl-co-methyl-2-methylpropylphenylsulfonate siloxane with 0.062 mmol·g−1 vinyl and 0.328 mmol·g−1 sulfonate, and 150 parts by weight of Silsoft 034 were placed in a Ross mixer. The mixture was stirred, and heated to 80° C. till the C-30 alpha olefin dissolved completely. Subsequently, the mixture was cooled down to 35° C., 1.02 parts by weight of a silanic hydrogen fluid represented by the average composition formula: $(CH_3)_3SiO((CH_3)_2SiO)_{20}((CH_3)HSiO)_{10}Si(CH_3)_3$ and 0.10 parts by weight of a Karstedt's catalyst containing 2% Platinum metal were added thereto and stirred till a uniform mixture was obtained. Then, the mixture was stirred at 35° C. for 15 minutes to facilitate hydrosilylation giving a solid cross-linked material, mixing was continued for another 45 minutes. The temperature was ramped to 80° C. and the solid material was mixed for 2 hours to ensure complete cross-linking/hydrosilylation. The solid polymer content of the cross linked material was found to be between 24-26%.

Example 8

90 parts by weight of the cross-linked material from Example 7 was blended with 110 parts by weight of Silsoft 034 (available from Momentive Performance Materials) in a Silverson mixer for 5 minutes at 5000 rpm. The material obtained was additionally subjected to a 5 minute blending cycle at 5000 rpm 4 times. The swelled material was then passed through a Microfluidizer three times to get a smooth, silky gel containing ~11.25% solid.

Example 9

90 parts by weight of the cross-linked material of Example 7 was blended with 110 parts by weight of 5 cps polydimethylsiloxane available from Momentive Performance Materials in a Silverson mixer for 5 minutes at 5000 rpm. The material obtained was additionally subjected to a 5 minute blending cycle at 5000 rpm 4 times. The swelled material was then passed through a Microfluidizer three times to get a smooth, silky gel containing ~11.25% solid.

Example 10

A three neck 100 mL flask was charged with 10.0 parts by weight of silanic hydrogen fluid represented by the average composition formula $(CH_3)_3SiO((CH_3)_2SiO)_{20}((CH_3)HSiO)_{10}Si(CH_3)_3$, 0.74 parts by weight of 10-undecenoic acid trimethylsilyl ester (UDA-E), and 10 ppm of a Karstedt's catalyst. The temperature of the resulting mixture was brought to 90° C., and the stirring was continued till the $^1$H NMR of the aliquot taken from the reaction mixture (2 hours) showed the complete disappearance of vinyl proton peaks of 10-undecenoic acid trimethylsilyl ester. After the completion of the reaction the product was indicated by the general formula $(CH_3)_3SiO((CH_3)_2SiO)_{20}((CH_3)HSiO)_{9.3}((CH_3)UDA\text{-}ESiO)_{0.7}Si(CH_3)_3$ and was stored at room temperature.

0.21 parts by weight of C-30 alpha olefin (from Chevron Phillips Company), 2.38 parts by weight vinyl end capped polydimethylsiloxane with 0.3 mmol·g−1 vinyl available from Momentive Performance Materials, 46.40 parts by weight vinyl end-capped polydimethylsiloxane with 0.05 mmol·g−1 vinyl available from Momentive Performance Materials, and 150 parts by weight of 5 cps polydimethylsiloxane available from Momentive Performance Materials were placed in a Ross mixer. The mixture was stirred, and heated to 80° C. till the C-30 alpha olefin dissolved completely. Subsequently, the mixture was cooled down to 35° C., 0.92 parts by weight of a silanic hydrogen fluid represented by the average composition formula: $(CH_3)_3SiO((CH_3)_2SiO)_{20}((CH_3)HSiO)_{10}Si(CH_3)_3$, 0.12 parts by weight of a modified silanic hydrogen fluid represented by the average general formula $(CH_3)_3SiO((CH_3)_2SiO)_{20}((CH_3)HSiO)_{9.3}((CH_3)UDA\text{-}ESiO)_{0.7}Si(CH_3)_3$ and 0.20 parts by weight of a Karstedt's catalyst containing 2% Platinum metal were added thereto and stirred till a uniform mixture was obtained. Then, the mixture was stirred at 35° C. for 15 minutes to facilitate hydrosilylation giving a solid cross-linked material, mixing was continued for another 45 minutes. The temperature was ramped to 80° C. and the solid material was mixed for 2 hours to ensure complete cross-linking/hydrosilylation. Afterwards, 0.2 parts by weight of water was added and the mixing was continued for another 2 hours. The solid polymer content of the cross linked material was found to be between 24-26%. The storage modulus G' of the cross linked material was 5800 Pa.

Example 11

20 parts by weight of the cross-linked material from Example 10 was blended with 80 parts by weight of 5 cps polydimethylsiloxane available from Momentive Performance Materials in a Silverson mixer for 5 minutes at 5000 rpm. The material obtained was additionally subjected to a 5 minute blending cycle at 5000 rpm 4 times. The swelled material was then passed through a Microfluidizer three times to get a smooth, silky gel containing ~5% solid.

Example 12

0.11 parts by weight of C-30 alpha olefin (from Chevron Phillips Company), 1.19 parts by weight vinyl end capped polydimethylsiloxane with 0.3 mmol·g−1 vinyl available from Momentive Performance Materials, 23.20 parts by weight vinyl end capped polydimethylsiloxane with 0.05 mmol·g−1 vinyl available from Momentive Performance Materials, and 75 parts by weight of 5 cps polydimethylsiloxane available from Momentive Performance Materials were placed in a Ross mixer. The mixture was stirred, and heated to 80° C. till the C-30 alpha olefin dissolved completely. Subsequently, the mixture was cooled down to 35° C., 0.51 parts by weight of a silanic hydrogen fluid represented by the average composition formula $(CH_3)_3SiO((CH_3)_2SiO)_{20}((CH_3)HSiO)_{9.3}((CH_3)UDA\text{-}ESiO)_{0.7}Si(CH_3)_3$ and 0.05 parts by weight of a Karstedt's catalyst containing 2% Platinum metal were added thereto and stirred till a uniform mixture was obtained. Then, the mixture was stirred at 35° C. for 15 minutes to facilitate hydrosilylation giving a solid cross-linked material, mixing was continued for another 45 minutes. The temperature was ramped to 80° C. and the solid material was mixed for 2 hours to ensure complete cross-linking/hydrosilylation. Afterwards, 0.2 parts by weight of water was added and the mixing was continued for another 2 hours. The solid polymer content of the cross linked material was found to be between 24-26%. The storage modulus G' of the cross linked material was 260 Pa.

Example 13

A three neck 100 mL flask was charged with 30.0 parts by weight of silanic hydrogen fluid represented by the average composition formula $(CH_3)_3SiO((CH_3)_2SiO)_{20}((CH_3)HSiO)_{10}Si(CH_3)_3$ and 2 drops of a Karstedt's catalyst containing 2% Platinum metal. The temperature of the resulting mixture was brought to 90° C. and then 17.0 parts by weight of 10-undecenoic acid trimethylsilyl ester (UDA-E) contained in a dropping funnel was added drop-wise to the above mixture. The stirring was continued till a $^1H$ NMR of the aliquot taken from the reaction mixture (3 hours) showed the complete disappearance of vinyl proton peaks of 10-undecenoic acid trimethylsilyl ester. After the completion of the reaction, the product indicated by the general formula $(CH_3)_3SiO((CH_3)_2SiO)_{20}((CH_3)HSiO)_5((CH_3)UDA\text{-}ESiO)_5Si(CH_3)_3$ was stored at room temperature.

0.21 parts by weight of C-30 alpha olefin (from Chevron Phillips Company), 2.30 parts by weight vinyl end capped polydimethylsiloxane with 0.3 mmol·g−1 vinyl available from Momentive Performance Materials, 44.50 parts by weight vinyl end capped polydimethylsiloxane with 0.05 mmol·g−1 vinyl available from Momentive Performance Materials, and 150 parts by weight of 5 cps polydimethylsiloxane available from Momentive Performance Materials were placed in a Ross mixer. The mixture was stirred, and heated to 80° C. till C-30 alpha olefin dissolved completely. Subsequently, the mixture was cooled down to 35° C., 3.0 parts by weight of a modified silanic hydrogen fluid represented by the average composition formula: $(CH_3)_3SiO((CH_3)_2SiO)_{20}((CH_3)HSiO)_5((CH_3)UDA\text{-}ESiO)_5Si(CH_3)_3$ and 0.20 parts by weight of a Karstedt's catalyst containing 2% Platinum metal were added thereto and stirred till a uniform mixture was obtained. Then, the mixture was stirred at 35° C. for 15 minutes to facilitate hydrosilylation giving a solid cross-linked material, mixing was continued for another 45 minutes. The temperature was ramped to 80° C. and the solid material was mixed for 2 hours to ensure complete cross-linking/hydrosilylation. Afterwards, 0.4 parts by weight of water was added and the mixing was continued for another 2 hours. The solid polymer content of the cross linked material was found to be between 24-26%. The storage modulus G' of the cross linked material was 280 Pa.

Example 14

0.21 parts by weight of C-30 alpha olefin (from Chevron Phillips Company), 2.30 parts by weight vinyl end capped polydimethylsiloxane with 0.3 mmol·g−1 vinyl available from Momentive Performance Materials, 44.50 parts by weight vinyl end capped polydimethylsiloxane with 0.05 mmol·g−1 vinyl available from Momentive Performance Materials, and 150 parts by weight of 5 cps polydimethylsiloxane available from Momentive Performance Materials were placed in a Ross mixer. The mixture was stirred, and heated to 80° C. till the C-30 alpha olefin dissolved completely. Subsequently, the mixture was cooled down to 35° C., 1.91 parts by weight of a silanic hydrogen fluid represented by the average composition formula: $(CH_3)_3SiO((CH_3)_2SiO)_{20}((CH_3)HSiO)_{10}Si(CH_3)_3$. 1.08 parts by weight of 10-undecenoic acid trimethylsilyl ester (UDA-E), and 0.10 parts by weight of a Karstedt's catalyst containing 2% Platinum metal were added thereto and stirred till a uniform mixture was obtained. Then, the mixture was stirred at 35° C. for 15 minutes to facilitate hydrosilylation giving a solid cross-linked material, mixing was continued for another 45 minutes. The temperature was ramped to 80° C. and the solid material was mixed for 2 hours to ensure complete cross-linking/hydrosilylation. Afterwards, 0.4 parts by weight of water was added and the mixing was continued for another 2 hours. The solid polymer content of the cross linked material was found to be between 24-26%. The storage modulus G' of the cross linked material was 5900 Pa.

Example 15

2.40 parts by weight vinyl end capped polydimethylsiloxane with 0.3 mmol·g−1 vinyl available from Momentive Performance Materials, 46.40 parts by weight vinyl end capped polydimethylsiloxane with 0.05 mmol·g−1 vinyl available from Momentive Performance Materials, and 150 parts by weight of 5 cps polydimethylsiloxane available from Momentive Performance Materials were placed in a Ross mixer. The mixture was stirred, and heated to 35° C. Subsequently, 0.98 parts by weight of a silanic hydrogen fluid represented by the average composition formula: $(CH_3)_3SiO((CH_3)_2SiO)_{20}((CH_3)HSiO)_{10}Si(CH_3)_3$, 0.35 parts by weight of 10-undecenoic acid trimethylsilyl ester (UDA-E), and 0.10 parts by weight of a Karstedt's catalyst containing 2% Platinum metal were added thereto and stirred till a uniform mixture was obtained. Then, the mixture was stirred at 35° C. for 15 minutes to facilitate hydrosilylation giving a solid cross-linked material, mixing was continued for another 45 minutes. The temperature was ramped to 80° C. and the solid material was mixed for 2 hours to ensure complete cross-linking/hydrosilylation. Afterwards, 0.4 parts by weight of water was added and the mixing was continued for another 2 hours. The solid polymer content of the cross linked material was found to be between 24-26%. The storage modulus G' of the cross linked material was 3300 Pa.

Example 16

0.21 parts by weight of C-30 alpha olefin (from Chevron Phillips Company), 46.90 parts by weight vinyl end capped polydimethyl-co-methyl-2-methylpropylphenylsulfonate siloxane with 0.062 mmol·g−1 vinyl and 0.328 mmol·g−1 sulfonate, and 150 parts by weight of 5 cps polydimethylsiloxane available from Momentive Performance Materials were placed in a Ross mixer. The mixture was stirred, and heated to 80° C. till the C-30 alpha olefin dissolved completely. Subsequently, the mixture was cooled down to 35° C., 3.0 parts by weight of a modified silanic hydrogen fluid represented by the average composition formula: $(CH_3)_3SiO((CH_3)_2SiO)_{20}((CH_3)HSiO)_5((CH_3)UDA-ESiO)_5Si(CH_3)_3$, and 0.10 parts by weight of a Karstedt's catalyst containing 2% Platinum metal were added thereto and stirred till a uniform mixture was obtained. Then, the mixture was stirred at 35° C. for 15 minutes to facilitate hydrosilylation giving a solid cross-linked material, mixing was continued for another 45 minutes. The temperature was ramped to 80° C. and the solid material was mixed for 2 hours to ensure complete cross-linking/hydrosilylation. Afterwards, 0.4 parts by weight of water was added and the mixing was continued for another 2 hours to give a highly viscous material. The solid polymer content of the cross linked material was found to be between 24-26%. The storage modulus G' of the cross linked material was 3.5 Pa.

Example 17

0.11 parts by weight of C-30 alpha olefin (from Chevron Phillips Company), 24.40 parts by weight vinyl end capped polydimethyl-co-methyl-2-methylpropylphenylsulfonate siloxane with 0.062 mmol·g−1 vinyl and 0.328 mmol·g−1 sulfonate, and 75 parts by weight of 5 cps polydimethylsiloxane available from Momentive Performance Materials were placed in a Ross mixer. The mixture was stirred, and heated to 80° C. till the C-30 alpha olefin dissolved completely. Subsequently, the mixture was cooled down to 35° C., 2.0 parts by weight of alpha-tocopherol, 0.51 parts by weight of a silanic hydrogen fluid represented by the average composition formula: $(CH_3)_3SiO((CH_3)_2SiO)_{20}((CH_3)HSiO)_{10}Si(CH_3)_3$ and 0.10 parts by weight of a Karstedt's catalyst containing 2% Platinum metal were added thereto and stirred till a uniform mixture was obtained. Then, the mixture was stirred at 35° C. for 15 minutes to facilitate hydrosilylation giving a solid cross-linked material, mixing was continued for another 45 minutes. Temperature was ramped to 55° C. and the solid material was mixed for 2 hours to ensure complete cross-linking/hydrosilylation. The solid polymer content of the cross linked material was found to be between 24-26%. The storage modulus G' of the cross linked material was 2500 Pa.

Example 18

0.077 parts by weight of C-30 alpha olefin (from Chevron Phillips Company), and 187.8 parts by weight of decamethylpentacyclosiloxane were placed in a Ross mixer. The mixture was stirred, and heated to 80° C. till the C-30 alpha olefin dissolved completely. Subsequently, the mixture was cooled down to 35° C., 36.76 parts by weight of 65,000 cst viscosity bis-vinyl polydimethylsiloxane available from Momentive Performance Materials, 24.51 parts by weight of a 10,000 cst viscosity bis-vinyl polydimethylsiloxane available from Momentive Performance Materials, 0.75 parts by weight of a silanic hydrogen fluid represented by the average composition formula: $(CH_3)_3SiO((CH_3)_2SiO)_{20}((CH_3)HSiO)_{10}Si(CH_3)_3$ and 0.13 parts by weight of a Karstedt's catalyst containing 2% Platinum metal were added thereto and stirred till a uniform mixture was obtained. Then, the mixture was stirred at 35° C. for 15 minutes to facilitate hydrosilylation giving a solid cross-linked material, mixing was continued for another 45 minutes. The temperature was ramped to 80° C. and the solid material was mixed for 2 hours to ensure complete cross-linking/hydrosilylation. The solid polymer content of the cross linked material was found to be between 24-26%.

20 parts by weight of cross-linked material described above containing 25% solid was blended with 80 parts by weight of decamethylpentacyclosiloxane and 30.0 parts by weight vinyl end capped polydimethyl-co-methyl-2-methylpropylphenylsulfonate siloxane with 0.062 mmol·g−1 vinyl and 0.328 mmol·g−1 sulfonate in a Silverson mixer for 5 minutes at 5,000 rpm. The material obtained was additionally subjected to a 5 minute blending cycle at 5,000 rpm 4 times. The swelled material was then passed through a Microfluidizer three times to get a viscous material.

Example 19

0.21 parts by weight of C-30 alpha olefin (from Chevron Phillips Company), 48.78 parts by weight vinyl end capped polydimethyl-co-methyl-2-methylpropylphenylsulfonate siloxane with 0.062 mmol·g−1 vinyl and 0.328 mmol·g−1 sulfonate, and 150 parts by weight of 5 cps polydimethylsiloxane available from Momentive Performance Materials were placed in a Ross mixer. The mixture was stirred, and heated to 80° C. till the C-30 alpha olefin dissolved completely. Subsequently, the mixture was cooled down to 35° C., 25.0 parts by weight of boron nitride, 1.02 parts by weight of a silanic hydrogen fluid represented by the average composition formula: $(CH_3)_3SiO((CH_3)_2SiO)_{20}((CH_3)HSiO)_{10}Si(CH_3)_3$, and 0.10 parts by weight of a Karstedt's catalyst containing 2% Platinum metal were added thereto and stirred till a uniform mixture was obtained. Then, the mixture was stirred at 35° C. for 15 minutes to facilitate hydrosilylation giving a solid cross-linked material, mixing was continued for another 45 minutes. The temperature was ramped to 80° C. and the solid material was mixed for 2 hours to yield a shiny white colored solid material. The storage modulus G' of the cross linked material was 4600 Pa.

Example 20

0.21 parts by weight of C-30 alpha olefin (from Chevron Phillips Company), 48.78 parts by weight vinyl end capped polydimethyl-co-methyl-2-methylpropylphenylsulfonate siloxane with 0.062 mmol·g−1 vinyl and 0.328 mmol·g−1 sulfonate, and 150 parts by weight of Silsoft 034 available from Momentive Performance Materials were placed in a Ross mixer. The mixture was stirred, and heated to 80° C. till the C-30 alpha olefin dissolved completely. Subsequently, the mixture was cooled down to 35° C., 25.0 parts by weight of boron nitride, 1.02 parts by weight of a silanic hydrogen fluid represented by the average composition formula: $(CH_3)_3SiO((CH_3)_2SiO)_{20}((CH_3)HSiO)_{10}Si(CH_3)_3$, and 0.10 parts by weight of a Karstedt's catalyst containing 2% Platinum metal were added thereto and stirred till a uniform mixture was obtained. Then, the mixture was stirred at 35° C. for 15 minutes to facilitate hydrosilylation giving a solid cross-linked material, mixing was continued for another 45 minutes. The temperature was ramped to 80° C. and the solid material was mixed for 2 hours to yield shiny white colored solid material. The storage modulus G' of the cross linked material was 3200 Pa.

Comparative Example 1

37.5 parts by weight of a 65000 cst viscosity bis-vinyl polydimethylsiloxane available from Momentive Performance Materials, 25.0 parts by weight of a 10,000 cst viscosity bis-vinyl polydimethylsiloxane available from Momentive Performance Materials, 0.35 parts by weight of an MQ resin hydride with 0.93% hydride available from Momentive Performance Materials, 0.13 parts by weight of a Karstedt's catalyst containing 2% Platinum metal, and 187.2 parts by weight of decamethylpentacyclosiloxane were placed in a Ross mixer. The mixture was stirred at 35° C. for 15 minutes to facilitate hydrosilylation giving a solid cross-linked material, mixing was continued for another 45 minutes. The mixture was stirred, and heated to 80° C. for 2 hours to ensure complete cross-linking/hydrosilylation. The solid polymer content of the cross linked material was found to be between 24-26%. The storage modulus G' of the cross linked material was 1300 Pa.

20 parts by weight of cross-linked material described above containing 25% solid was blended with 80 parts by weight of decamethylpentacyclosiloxane in Silverson mixer for 5 minutes at 5000 rpm. The material obtained was additionally subjected to a 5 minute blending cycle at 5000 rpm 4 times. The swelled material was then passed through a Microfluidizer three times to get a gel containing ~5% solid.

Comparative Example 2

0.077 parts by weight of C-30 alpha olefin (from Chevron Phillips Company), and 187.8 parts by weight of decamethylpentacyclosiloxane were placed in a Ross mixer. The mixture was stirred, and heated to 80° C. till the C-30 alpha olefin dissolved completely. Subsequently, the mixture was cooled down to 35° C., 36.76 parts by weight of 65,000 cst viscosity bis-vinyl polydimethylsiloxane available from Momentive Performance Materials, 24.51 parts by weight of a 10,000 cst viscosity bis-vinyl polydimethylsiloxane available from Momentive Performance Materials, 0.75 parts by weight of a silanic hydrogen fluid represented by the average composition formula: $(CH_3)_3SiO((CH_3)_2SiO)_{20}((CH_3)HSiO)_{10}Si(CH_3)_3$ and 0.13 parts by weight of a Karstedt's catalyst containing 2% Platinum metal were added thereto and stirred till uniform mixture was obtained. Then, the mixture was stirred at 35° C. for 15 minutes to facilitate hydrosilylation giving a solid cross-linked material, mixing was continued for another 45 minutes. The temperature was ramped to 80° C. and the solid material was mixed for 2 hours to ensure complete cross-linking/hydrosilylation. The solid polymer content of the cross linked material was found to be between 24-26%.

20 parts by weight of the above described cross-linked material containing 25% solid was blended with 80 parts by weight of decamethylpentacyclosiloxane in Silverson mixer for 5 minutes at 5,000 rpm. The material obtained was additionally subjected to a 5 minute blending cycle at 5,000 rpm 4 times. The swelled material was then passed through a Microfluidizer three times to get a gel containing ~5% solid-viscosity 5,000 cps. The storage modulus G' of the cross linked material was 50 Pa.

Compatibility Studies:

Compatibility studies between the cross-polymer gel of example 1 and comparative example 2 were carried out by blending the gels with various personal care ingredients like water, glycerin, isopropyl myristate, polar organic oils, $TiO_2$, boron nitride, Nano clay etc. in 1:1 proportion. FIG. 1 clearly demonstrates that the particle size of optically opaque material ($TiO_2$, BN, & Nano clay) is much smaller & particles are well dispersed in blends of Example 1 than in Comparative Example 2.

| Solvent/Pigments | Comparative Example 2 | Example 1 |
|---|---|---|
| Water | Incompatible | Incompatible |
| Glycerin | Incompatible | Compatible |
| Isopropyl myristate | Compatible | Compatible |
| Olive Oil | Compatible | Compatible |
| Titanium dioxide | Incompatible | Compatible |
| Boron Nitride | Incompatible | Compatible |
| Nanoclay | Incompatible | Compatible |

FIG. 1 below shows the microscopy images of blends of Example 1 & Comparative Example 2 gels with Titanium dioxide, Boron nitride & Nano clay Cosmetic Formulations:

Sun mousse:

| Ingredients | Wt % | Wt % | Source |
|---|---|---|---|
| Example 1 | 75 | 0 | |
| Comparative Example 2 | 0 | 75 | |
| Silsoft 034 Organosilicone fluid | 5 | 5 | Momentive Performance Materials Inc. |
| SF 1202 (cyclopentasiloxane) | 3 | 3 | Momentive Performance Materials Inc. |
| SR1000 (MQ Resin) | 2 | 2 | Momentive Performance Materials Inc. |
| Titanium Dioxide | 15 | 15 | |
| | 100 | 100 | |

Figure 2:
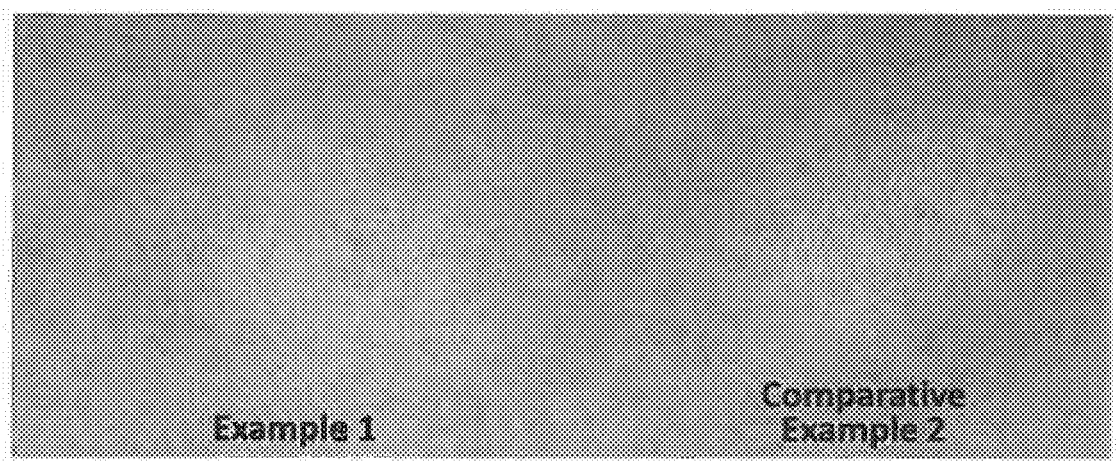
FIG. 2 is a photograph of a Sun Mousse formulation prepared from Example 1 & Comparative Example 2 gels applied on the inner side of a forearm.

Procedure:

i. Dissolve SR 1000 in SF1202 and Silsoft 034 ii. Add above mixture to Gel 1 and blend at 600 rpm for 5 minutes iii. Add TiO2 and blend all materials at 600 rpm for 10 minutes or until uniform iv. Mix above material for 10 minutes in Flack-Tek FIG. 2 shown below shows a photograph of Sun Mousse prepared from Example 1 & Comparative Example 2 gels applied on the inner side of a forearm. It is clear from the FIG. 2 that the sun mousse prepared from Example 1 gel is less whitening than the comparative Example 2 sun mousse.

Sunscreen Lotion:

| Part | Ingredient | Wt % | Wt % | Source |
|---|---|---|---|---|
| A | Silsoft 034 | 3 | 3 | Momentive Performance Materials Inc. |
| | SR 1000 (50%) | 1 | 1 | Momentive Performance Materials Inc. |
| | Example 1 | 20 | 0 | |
| | Comparative Example 2 | 0 | 20 | |
| | PEG-100 Glycerol Stearate | 3 | 3 | BASF |
| | Stearyl Alcohol | 1.5 | 1.5 | |
| | Stearic Acid | 1 | 1 | |
| | Cetiol B (Dibutyl Dipate) | 0.6 | 0.6 | BASF |
| | Benzophhenone-3 (2-Hydroxy-4-Methoxybenzophhenone) | 2.0 | 2.0 | |
| | Avobenzene (Eusolex 9020) | 1.5 | 1.5 | Merck |

-continued

| Part | Ingredient | Wt % | Wt % | Source |
|---|---|---|---|---|
| B | Demineralized Water | 55.68 | 55.68 | |
| | Carbopol U21 hydrophobically modified cross-linked acrylate copolymer | 0.1 | 0.1 | Lubrizol |
| | Glycerin | 2.0 | 2.0 | |
| C | Triethanolamine | 0.1 | 0.1 | |
| D | Demineralized Water | 5.12 | 5.12 | |
| | Niacinamide | 2.0 | 2.0 | |
| E | Panthanol | 1 | 1 | Sigma Aldrich |
| | Euxyl 9010 | 0.1 | 0.1 | Schülke |
| | Tocopherol Acetate | 0.3 | 0.3 | |
| | | 100 | 100 | |

Procedure:
i. PART A; Premix Silsoft 034 and SR 1000 in a main vessel; add remaining ingredients of PART A
ii. Heat Part A up to 75° C., under stirring
iii. Part B: in a separate vessel add Carbopol U21 in given amount of water, after dispersion, allow it to wet then mix well: add glycerin and mix well.
iv. Heat Part B up to 75° C., under stirring
v. At 75° C., Add Part B in to Part A with high speed stirring, stir well for 5 min.
vi. Add PART C into PART AB and mix well for 5 min.
vii. Cool the batch the under stirring up to 50° C.
viii. Premix Part D in a separate vessel, add it in to PART ABC and mix well
ix. Add PART E ingredients as per given order and mix well after each addition
x. Mix the batch for 5 to 8 min. and finish the process.

Liquid Foundation:

| Part | Ingredient | Wt % | Wt % | Source |
|---|---|---|---|---|
| A | Example 1 | 5 | 0 | |
| | Comparative Example 2 | 0 | 5 | |
| | SF 1202 (cyclopentasiloxane) | 10 | 10 | Momentive Performance Materials Inc. |
| | SF 1540 40% solution of a polyether silicone copolymer dispersed in cyclopentasiloxane | 4 | 4 | Momentive Performance Materials Inc. |
| | Crodamol GTCC Saturated polyol ester | 4 | 4 | Croda |
| B | Pigment Blend (TiO2(79.6%) + Iron Oxide Red (9.60%) + Iron Oxide Yellow (9.80%) + Iron Oxide Black (1%)) | 6 | 6 | |
| | Tospearl 2000B | 2 | 2 | Momentive Performance Materials Inc. |
| C | Water | 64 | 64 | |
| | NaCl | 1 | 1 | |
| | SF 1188A Copolymer of polydimethylsiloxane and a polyoxyalkylene ether | 1 | 1 | Momentive Performance Materials Inc. |
| | Glycerin | 3 | 3 | |
| | | 100 | 100 | |

Figure 3:
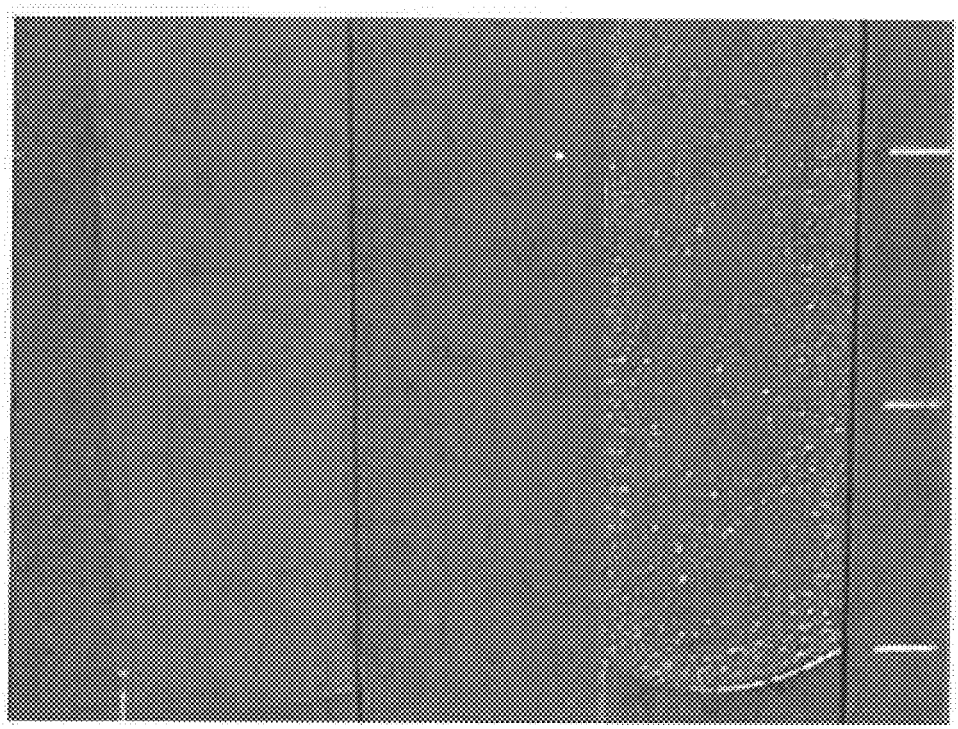
FIG. 3 is a photograph showing the difference in the pigment dispersion & color between liquid foundations made from Example 1 & Comparative example 2 gels.

Procedure:
i. Mix all ingredients of phase A, homogenize
ii. Mix all ingredients of phase B,
iii. Slowly add phase B to phase A while mixing well FIG. 3 shown below is a photograph showing the difference in the pigment dispersion & color between liquid foundations made from Example 1 & Comparative example 2 gels. Liquid foundation made from Example 1 gel was more spreadable than the liquid foundation made from Comparative Example 2, also from FIG. 3 it is clear that the pigments were well dispersed in formulation with Example 1 than with Comparative Example 2.

The above noted examples clearly demonstrate that all of the ionic silicone based compositions have shown significant improvement over traditional non-ionic silicone based composition with respect to the compatibility with hydrophilic and lipophilic ingredients, pigment dispersion and sensory feeling.

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention but that the invention will include all embodiments falling within the scope of the appended claims.

The invention claimed is:

1. A personal care composition comprising an oil and an ionically-modified cross-linked silicone network gel therein, and a particulate additive the ionically-modified cross-linked silicone network gel being derived from the process which comprises reacting:
   (i) a silicone hydride bearing at least two Si—H residues,
   (ii) at least one olefinic compound with two or more unsaturated radicals,
   (iii) catalytically effective amount of precious metal catalyst, and
   (iv) optionally, a solvent for swelling the ionically modified cross-linked silicone network;
subject to the limitation that at least one of (i), (ii) or (iv) is selected from the ionically modified silicone of the general formula (I):

$$M^1_a M^2_b M^3_c D^1_d D^2_e D^3_f T^1_g T^2_h T^3_i Q_j \qquad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$
where $R^1$, $R^2$, $R^3$, $R^5$, $R^6$, $R^8$, $R^9$, $R^{10}$, $R^{11}$, $R^{13}$, $R^{15}$, $R^{16}$ are aliphatic, aromatic or fluoro containing monovalent hydrocarbon radicals containing from 1 to about 60 carbon atoms,
where $R^4$, $R^{12}$, $R^{17}$ are monovalent or multivalent radical bearing ion-pairs, where $R^7$, $R^{14}$ and $R^{18}$ are independently selected from hydrogen, —$OR^{20}$ or hydrosilylation effective unsaturated monovalent radicals wherein $R^{20}$ is selected from hydrogen and monovalent hydrocarbon radical of from 1 to about 60 carbon atoms, where the subscript a, b, c, d, e, f, g, h, i, j are zero or positive subject to the following limitations: the sum a+b+c+d+e+f+g+h+i+j is greater than or equal to 2 and less than or equal to 6000, b+e+h is greater than 0 to produce the crosslinked ionic silicone network; and, shearing the crosslinked ionic silicone network during and/or after the reacting step with at least solvent (iv) to form the crosslinked ionic silicone network gel.

2. The personal care composition of claim 1 wherein the ionic radicals $R^4$, $R^{12}$, $R^{17}$ comprises the monovalent residues having the general formula (II):

(II)

where A is a spacing group selected from a divalent hydrocarbon and hydrocarbonoxy group, where superscripts n and y are independently from 1 to 6 and x is a product of n and y, where I is an ionic group selected from the group consisting of sulfonate —$SO_3^-$, sulfate —$OSO_3^-$, carboxylate —$COO^-$, phosphonate —$PO_3^{2-}$ and phosphate —$OPO_3^{2-}$ group, where M is hydrogen or a cation independently selected from alkali metals, alkaline earth metals, rare earth metals, transition metals, metals, metal complexes, quaternary ammonium, polymeric organic or inorganic cations and phosphonium groups.

3. The personal care composition of claim 1 wherein the ionic radicals $R^4$, $R^{12}$, $R^{17}$ comprises monovalent residues having the general formula (III):

—R'—NR''$_2^+$—R'''-I (III)

where R' is a divalent hydrocarbon radical containing from 1 to about 60 carbon atoms, where R'' is monovalent hydrocarbon radical containing from 1 to about 60 carbon atoms, and where R''' is divalent hydrocarbon radical containing from 2 to about 20 carbon atoms, and, I is an ionic group selected from the group consisting of sulfonate —$SO_3^-$, sulfate —$OSO_3^-$, carboxylate —$COO^-$, phosphonate —$PO_3^{2-}$ group and phosphate —$OPO_3^{2-}$ group.

4. The personal care composition of claim 1, wherein at least one of the ionic radicals $R^4$, $R^{12}$, $R^{17}$ comprise the multivalent ion pairs.

5. The personal care composition of claim 1 wherein the ionically-modified cross-linked silicone network gel is made by reacting:

(i) an ionically modified silicone hydride bearing at least two Si—H residues and having the general formula (IV):

(IV)

wherein:
$M^1=R^1R^2R^3SiO_{1/2}$
$M^2=R^4R^5R^6SiO_{1/2}$
$M'=R^HR^8R^9SiO_{1/2}$
$D^1=R^{10}R^{11}SiO_{2/2}$
$D^2=R^{12}R^{13}SiO_{2/2}$
$D'=R^HR^{15}SiO_{2/2}$
$T^1=R^{16}SiO_{3/2}$
$T^2=R^{17}SiO_{3/2}$
$T'=R^HSiO_{3/2}$
$Q=SiO_{4/2}$ where $R^H$ is a hydrogen atom, each $R^1$, $R^2$, $R^3$, $R^5$, $R^6$, $R^8$, $R^9$, $R^{10}$, $R^{11}$, $R^{13}$, $R^{15}$, $R^{16}$ are independently selected from an aliphatic, aromatic or fluoro containing monovalent hydrocarbon radicals containing from 1 to about 60 carbon atoms, where $R^4$, $R^{12}$, $R^{17}$ are monovalent or multivalent radical bearing ion-pairs, (ii) at least one olefinic compound with two or more unsaturated radicals, (iii) an effective amount of precious metal catalyst, and (iv) optionally, a solvent suitable for swelling the ioically modified crosslinked silicone network, where the subscript a, b, c, d, e, f, g, h, i, j are zero or positive subject to the following limitations: the sum a+b+c+d+e+f+g+h+i+j is greater than or equal to 2 and less than or equal to 6000, b+e+h is greater than 0 and c+f+i is ≥2.

6. The personal care composition of claim 5 wherein the at least one olefinic compound comprises a blend of at least one multifunctional olefin and at least one mono-functional olefin.

7. The personal care composition of claim 1 wherein the ionically modified cross-linked silicone network gel is made by reacting:

(i) a silicone hydride bearing at least two Si—H residues, (ii) at least one olefinic compound containing two or more unsaturated radicals wherein the at least one olefinic compound comprises at least one ionically modified olefinic silicone having the general formula (V):

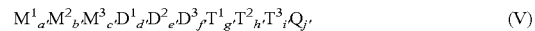

(V)

wherein:
$M^1=R^1R^2R^3SiO_{1/2}$
$M^2=R^4R^5R^6SiO_{1/2}$
$M^3=R^OR^8R^9SiO_{1/2}$
$D^1=R^{10}R^{11}SiO_{2/2}$
$D^2=R^{12}R^{13}SiO_{2/2}$
$D^3=R^OR^{15}SiO_{2/2}$
$T^1=R^{16}SiO_{3/2}$
$T^2=R^{17}SiO_{3/2}$
$T^3=R^OSiO_{3/2}$
$Q=SiO_{4/2}$ where each $R^O$ is independently selected from an olefinic radical containing from 2 to about 20 carbon atoms and an alkyne residue containing monovalent radicals of from about 2 to about 20 carbon atoms, where each of $R^1$, $R^2$, $R^3$, $R^5$, $R^6$, $R^8$, $R^9$, $R^{10}$, $R^{11}$, $R^{13}$, $R^{15}$, $R^{16}$ are independently selected from an aliphatic, aromatic or fluoro containing monovalent hydrocarbon radicals containing from 1 to about 60 carbon atoms, where $R^4$, $R^{12}$, $R^{17}$ are monovalent or multivalent radical bearing ion-pairs, where the subscripts a', b', c', d', e', f', g', h', i', j' are zero or positive subject to the following limitations: the sum a'+b'+c'+d'+e'+f'+g'+h'+i'+j' is greater than or equal to 2 and less than or equal to 6000, b'+e'+h' is greater than 0 and c'+f'+i' is ≥2, (iii) an effective amount of precious metal catalyst, and (iv) optionally, a solvent for swelling the ionically modified crosslinked silicone network.

8. The personal care composition of claim 7 wherein the at least one olefinic compound comprises a combination of a non-silicone olefin and an organo-modified silicone olefin of the general structure (V).

9. The personal care composition of claim 1 wherein the ionically-modified cross-linked silicone network gel is made by reacting:
(i) a silicone hydride bearing at least two Si—H residues,
(ii) at least one olefinic compound with two or more unsaturated radicals,
(iii) an effective amount of precious metal catalyst, and
(iv) a solvent for swelling the ionically-modified cross-linked silicone network comprising an ionically modified silicone copolymer having the general formula (VI):

$$M^7_\alpha M^8_\beta D^7_\chi D^8_\delta T^7_\epsilon T^8_\phi Q_\gamma \quad (VI)$$

wherein:
$M^7 = R^1R^2R^3SiO_{1/2}$
$M^8 = R^4R^5R^I SiO_{1/2}$
$D^7 = R^6R^7 SiO_{2/2}$
$D^8 = R^8R^I SiO_{2/2}$
$T^7 = R^9 SiO_{3/2}$
$T^8 = R^I SiO_{3/2}$
$Q = SiO_{4/2}$,
and where each of $R^1$, $R^2$, $R^3$, $R^5$, $R^6$, $R^8$ and $R^9$ are independently selected from an aliphatic, aromatic or fluoro containing monovalent hydrocarbon radicals containing from 1 to about 60 carbon atoms,
each $R^I$ is an ion pair,
and the subscripts $\alpha$, $\beta$, $\chi$, $\delta$, $\epsilon$, $\phi$, and $\gamma$ are zero or positive subject to the following limitations: $2 \leq \alpha+\beta+\chi+\delta+\epsilon+\phi+\gamma \leq 6000$; and $\beta+\delta+\phi > 0$.

10. The personal care composition of claim 1 wherein the precious metal catalyst (iii) is at least one catalyst selected from the group consisting of rhodium, ruthenium, palladium, osmium, iridium and platinum catalysts.

11. The personal care composition of claim 10 wherein the precious metal catalyst (iii) is a platinum catalyst.

12. The personal care composition of claim 1 wherein the solvent (iv) is at least one selected from silicone fluids, hydrocarbon fluids, esters, alcohols, fatty alcohols, glycols, organic waxes and organic oils.

13. The personal care composition of claim 1 wherein the solvent (iv) is a hydrophilic emollient selected from the group consisting of glycerine, sorbitol, aqueous solution of moisturizing additives and combinations thereof.

14. The personal care composition of claim 1 further comprising a cosmetically acceptable carrier selected from the group consisting of an aqueous medium, a non-aqueous medium and combination thereof.

15. The personal care composition of claim 1 wherein the composition further comprises a fragrance, an active, a biocide and combinations thereof.

16. The personal care composition of claim 1 wherein the particulate additive is selected from inorganic particulates, polymeric latexes, and pigments.

17. The personal care composition of claim 1 further comprising an aqueous phase.

18. The personal care composition of claim 1 wherein the composition is a homogenous system selected from aqueous or non-aqueous formulations.

19. The personal care composition of claim 1 wherein the ionically-modified silicone cross-polymer network gel can bind and slow release cosmetic actives.

20. A personal care application comprising the personal care composition of claim 1 wherein the personal care application is selected from the group consisting of deodorants, antiperspirants, antiperspirant/deodorants, shaving products, skin lotions, moisturizers, toners, bath products, cleansing products, hair care products, manicure products, protective creams, color cosmetics, and other personal care formulations where silicone components have been conventionally added, as well as drug delivery systems for topical application of medicinal compositions that are to be applied to the skin.

21. A process for preparing a personal care composition comprising an oil and an ionically-modified cross-linked silicone network gel therein, and a particulate additive the ionically-modified cross-linked silicone network gel being derived from the process which comprises reacting:
(i) a silicone hydride bearing at least two Si—H residues,
(ii) at least one olefinic compound with two or more unsaturated radicals,
(iii) a catalytically effective amount of precious metal catalyst, and
(iv) optionally, a solvent for swelling the ionically-modified cross-linked silicone network;
subject to the limitation that at least one of (i), (ii) or (iv) is selected from the ionically modified silicone of general formula (I):

$$M^1_a M^2_b M^3_c D^1_d D^2_e D^3_f T^1_g T^2_h T^3_i Q_j \quad (I)$$

wherein:
$M^1 = R^1R^2R^3 SiO_{1/2}$
$M^2 = R^4R^5R^6 SiO_{1/2}$
$M^3 = R^7R^8R^9 SiO_{1/2}$
$D^1 = R^{10}R^{11} SiO_{2/2}$
$D^2 = R^{12}R^{13} SiO_{2/2}$
$D^3 = R^{14}R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$
where $R^1$, $R^2$, $R^3$, $R^5$, $R^6$, $R^8$, $R^9$, $R^{10}$, $R^{11}$, $R^{13}$, $R^{15}$, $R^{16}$ are aliphatic, aromatic or fluoro containing monovalent hydrocarbon radicals containing from 1 to about 60 carbon atoms,
where $R^4$, $R^{12}$, $R^{17}$ are each independently monovalent or multi-valent radical bearing ion-pairs,
where $R^7$, $R^{14}$ and $R^{18}$ are independently selected from hydrogen, —$OR^{20}$ or unsaturated monovalent radicals wherein $R^{20}$ is selected from hydrogen, monovalent hydrocarbon radical of from 1 to about 60 carbon atoms,
where the subscript a, b, c, d, e, f, g, h, i, j are zero or positive subject to the following limitations: the sum a+b+c+d+e+f+g+h+i+j is greater than or equal to 2 and less than or equal to 6000, b+e+h is greater than 0, to produce an ionically-modified cross-linked silicone network; and,
shearing the ionically-modified cross-linked silicone network using at least a solvent (iv) to provide the ionically-modified cross-linked silicone network gel.

22. The process according to claim 21, wherein the process further comprises use of a hydrosilylation inhibitor to inhibit the reaction of (i) and (ii).

23. The personal care composition of claim 1 wherein the shearing step is conducted at a rate of up to about 5,000 rpm.

24. The personal care composition of claim 1 wherein the particulate additive is selected from the group consisting of talc, kaolin, starch, modified starch, mica, nylon, clays, bentonite and organo-modified clays.

25. The personal care composition of claim 1 wherein the particulate additive is selected from the group consisting of titanium oxide, boron nitride, and nanoclay.

26. The process of claim 21 wherein the particulate additive is selected from the group consisting of talc, kaolin, starch, modified starch, mica, nylon, clays, bentonite and organo-modified clays.

27. The process of claim 21 wherein the particulate additive is selected from the group consisting of titanium oxide, boron nitride, and nanoclay.

\* \* \* \* \*